(12) United States Patent
Usta et al.

(10) Patent No.: US 9,911,927 B2
(45) Date of Patent: Mar. 6, 2018

(54) COMPOUNDS HAVING SEMICONDUCTING PROPERTIES AND RELATED COMPOSITIONS AND DEVICES

(71) Applicant: Flexterra, Inc., Skokie, IL (US)

(72) Inventors: Hakan Usta, Kayseri (TR); Damien Boudinet, Zhubei (TW); Jordan Quinn, Mundelein, IL (US); Antonio Facchetti, Chicago, IL (US)

(73) Assignee: Flexterra, Inc., Skokie, IL (US)

( * ) Notice: Subject to any disclaimer, the term of this patent is extended or adjusted under 35 U.S.C. 154(b) by 0 days.

(21) Appl. No.: 15/137,939

(22) Filed: Apr. 25, 2016

(65) Prior Publication Data

US 2016/0351832 A1  Dec. 1, 2016

Related U.S. Application Data

(63) Continuation of application No. 13/608,976, filed on Sep. 10, 2012, now abandoned.

(60) Provisional application No. 61/533,785, filed on Sep. 12, 2011.

(51) Int. Cl.

| | |
|---|---|
| *H01L 51/54* | (2006.01) |
| *H01L 51/00* | (2006.01) |
| *C07D 493/04* | (2006.01) |
| *C07D 495/04* | (2006.01) |
| *H01L 51/05* | (2006.01) |
| *H01L 51/52* | (2006.01) |

(52) U.S. Cl.
CPC ........ *H01L 51/0074* (2013.01); *C07D 493/04* (2013.01); *C07D 495/04* (2013.01); *H01L 51/052* (2013.01); *H01L 51/0516* (2013.01); *H01L 51/0525* (2013.01); *H01L 51/0541* (2013.01); *H01L 51/0545* (2013.01); *H01L 51/0558* (2013.01); *H01L 51/0562* (2013.01); *H01L 51/5296* (2013.01)

(58) Field of Classification Search
CPC .. C07D 491/00; C07D 491/02; C07D 491/04; C07D 491/06; C07D 495/00; C07D 495/02; C07D 495/04; C07D 495/06; C07C 15/20; C07C 15/38; C07C 15/56; C07C 15/62; C07C 2103/00; C07C 2103/02; C07C 2103/40; C07C 2103/42; C07C 2103/44; C07C 2103/48; C07C 2103/52; C07C 2103/54; H01L 51/0032; H01L 51/005; H01L 51/0052; H01L 51/0054; H01L 51/0055; H01L 51/0056; H01L 51/0071; H01L 51/0073; H01L 51/0074; H01L 51/05; H01L 51/0504; H01L 51/0508; H01L 51/0533; H01L 51/052; H01L 51/0529; H01L 51/50

USPC ......... 428/690, 691, 411.4, 36, 917; 427/58, 427/66; 313/500–512; 257/40, 88–104, 257/E51.001–E51.052; 252/301.16–301.35; 549/41, 456, 457; 570/183, 129, 128; 585/26

See application file for complete search history.

(56) References Cited

U.S. PATENT DOCUMENTS

| | | | |
|---|---|---|---|
| 2009/0043113 A1 | 2/2009 | Park et al. | 549/41 |
| 2010/0032655 A1 | 2/2010 | Takimiya et al. | 257/40 |
| 2011/0210319 A1* | 9/2011 | Nakano | C07C 15/20 |
| | | | 257/40 |
| 2011/0303910 A1* | 12/2011 | Kuwabara | C07C 319/14 |
| | | | 257/40 |
| 2012/0161110 A1 | 6/2012 | Wu et al. | 257/40 |
| 2012/0190868 A1 | 7/2012 | Miyata et al. | 549/41 |

FOREIGN PATENT DOCUMENTS

| | | | | |
|---|---|---|---|---|
| EP | 2098527 | 9/2009 | | |
| JP | 2009283786 | 3/2009 | | |
| JP | WO2010098372 A1 * | 9/2010 | ........... | C07C 319/14 |
| JP | 2011134757 | 7/2011 | | |
| WO | 2008/047896 | 4/2008 | | |
| WO | 2008/050726 | 5/2008 | | |

OTHER PUBLICATIONS

J.W. Cook and A.M. Robinson, "Polycyclic Aromatic Hydrocarbons. Part XVII. Completion of the Synthesis of the Twelve Monomethyl-1 : 2-benzanthracenes." *Journal of the Chemical Society (Resumed)*, pp. 505-513 (1938).

Kang et al., "Alkylated Dinaphtho[2,3-b:2',3'-f]Thieno[3,2-b]Thiophenes ($C_n$-DNTTs): Organic Semiconductors for High-Performance Thin Film Transistors," *Advanced Materials*, vol. 23, pp. 1222-1225. (Aug. 20, 2010).

Niimi et al., "General Synthesis of Dinaphtho-[2,3-b:2',3'-f]thieno[3,2-b]thiophene (DNTT) Derivatives," *Organic Letters*, vol. 13, No. 13, pp. 3430-3433 (May 31, 2011).

Nakayama et al., "Patternable Solution-Crystallized Organic Transistors with High Charge Carrier Mobility," *Advanced Materials*, vol. 23, pp. 1626-1629 (Feb. 10, 2011).

* cited by examiner

*Primary Examiner* — Andrew K Bohaty

(74) *Attorney, Agent, or Firm* — McDonnell Boehnen Hulbert & Berghoff LLP

(57) ABSTRACT

Disclosed are new compounds having semiconducting properties. Such compounds can be processed in solution-phase at a temperature of less than about 50° C. into thin film semiconductors that exhibit high carrier mobility and/or good current modulation characteristics.

13 Claims, 2 Drawing Sheets

COMPOUNDS HAVING SEMICONDUCTING PROPERTIES AND RELATED COMPOSITIONS AND DEVICES

CROSS REFERENCE TO RELATED APPLICATIONS

This application is a continuation of U.S. patent application Ser. No. 13/608,976, filed on Sep. 10, 2012, which claims priority to and the benefit of U.S. Provisional Patent Application Ser. No. 61/533,785, filed on Sep. 12, 2011, the disclosure of each of which is incorporated by reference herein in its entirety.

BACKGROUND

Organic optoelectronic devices such as organic thin film transistors (OTFTs), organic light emitting diodes (OLEDs), organic light emitting transistors (OLETs), printable circuits, organic photovoltaic devices, capacitors and sensors are fabricated using small molecule or polymeric semiconductors as their active components. To achieve high speed performance and efficient operation, it is desirable that both the p-type and n-type semiconductor materials in these organic semiconductor-based devices exhibit high charge carrier mobility ($\mu$) and stability under ambient conditions, and can be processed in a cost-effective manner.

Accordingly, the art continues to desire new organic semiconductors, particularly those having good stability, processing properties, and/or charge transport characteristics in ambient conditions.

SUMMARY

In light of the foregoing, the present teachings relate to new semiconducting compounds that can exhibit properties such as good charge transport characteristics under ambient conditions, chemical stability, low-temperature processability, large solubility in common solvents, and processing versatility. As a result, semiconductor devices such as thin film transistors and light emitting transistors that incorporate the present compounds as the semiconductor layer can have high performance under ambient conditions, for example, demonstrating one or more of large electron mobilities, low threshold voltages, and high current on-off ratios.

In various embodiments, the present teachings provide compounds of formula I:

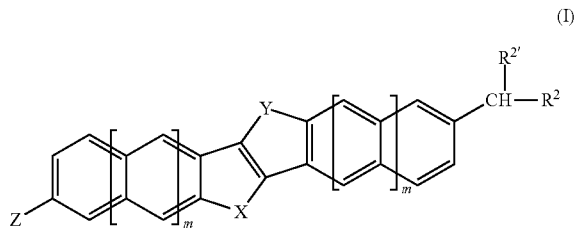

(I)

wherein:
X is selected from S, O, and CH=CH;
Y is selected from S, O, and CH=CH;
Z is H or $CHR^1R^{1'}$;
$R^1$, $R^{1'}$, $R^2$, and $R^{2'}$ independently are selected from a linear $C_{1-40}$ alkyl group, a linear $C_{2-40}$ alkenyl group, and a linear $C_{1-40}$ haloalkyl group; and m, at each occurrence, independently is selected from 0, 1, 2, 3, and 4.

The present teachings also provide methods of preparing semiconductor materials, as well as various compositions, composites, and devices that incorporate the compounds and semiconductor materials disclosed herein.

The foregoing as well as other features and advantages of the present teachings will be more fully understood from the following figures, description, examples, and claims.

BRIEF DESCRIPTION OF THE DRAWINGS

It should be understood that the drawings described below are for illustration purpose only. The drawings are not necessarily to scale, with emphasis generally being placed upon illustrating the principles of the present teachings. The drawings are not intended to limit the scope of the present teachings in any way.

DETAILED DESCRIPTION

Figure 1:
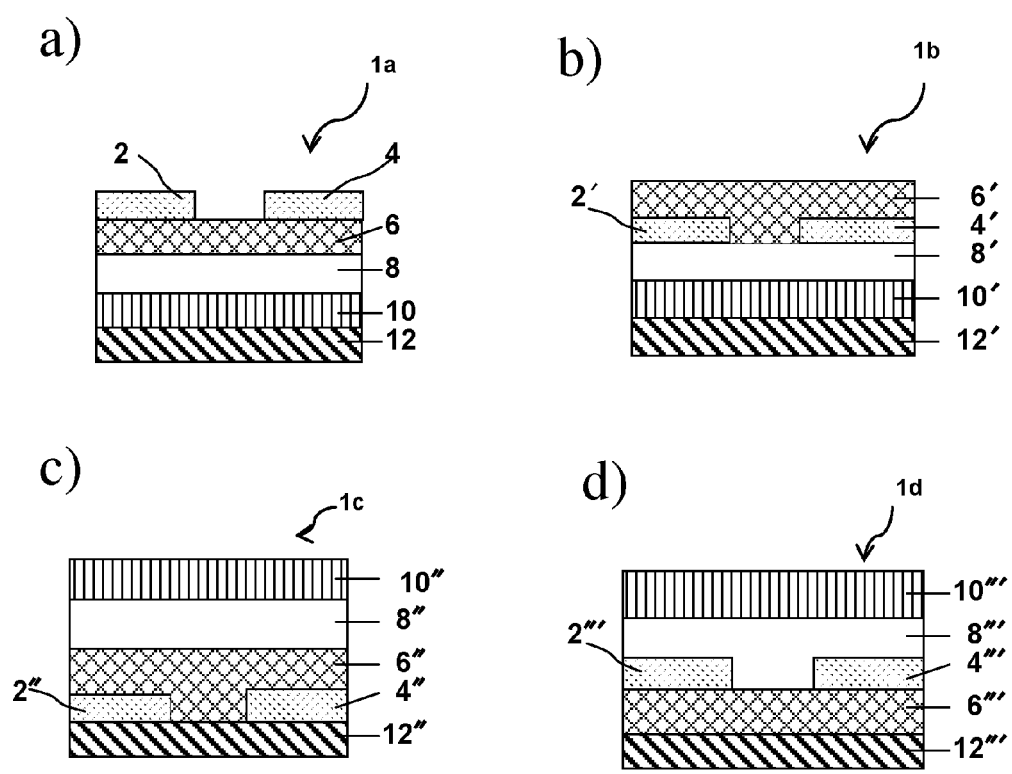
FIG. 1 illustrates four different configurations of thin film transistors: bottom-gate top contact (a), bottom-gate bottom-contact (b), top-gate bottom-contact (c), and top-gate top-contact (d); each of which can be used to incorporate compounds of the present teachings.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl).

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula $-C_sH_{2s+1-t}X^0_t$, where $X^0$, at each occurrence, is F, Cl, Br or I, s is an integer in the range of 1 to 40, and t is an integer in the range of 1 to 81, provided that t is less than or equal to 2s+1. Haloalkyl groups that are not perhaloalkyl groups can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group).

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

It is specifically contemplated that the depiction of one stereoisomer includes any other stereoisomer and any stereoisomeric mixtures unless specifically stated otherwise.

As used herein, a "p-type semiconductor material" or a "p-type semiconductor" refers to a semiconductor material having holes as the majority current carriers. In some embodiments, when a p-type semiconductor material is deposited on a substrate, it can provide a hole mobility in excess of about $10^{-5}$ $cm^2/Vs$. In the case of field-effect devices, a p-type semiconductor can also exhibit a current on/off ratio of greater than about 10.

As used herein, an "n-type semiconductor material" or an "n-type semiconductor" refers to a semiconductor material having electrons as the majority current carriers. In some embodiments, when an n-type semiconductor material is deposited on a substrate, it can provide an electron mobility in excess of about $10^{-5}$ $cm^2/Vs$. In the case of field-effect devices, an n-type semiconductor can also exhibit a current on/off ratio of greater than about 10.

As used herein, "mobility" refers to a measure of the velocity with which charge carriers, for example, holes (or units of positive charge) in the case of a p-type semiconductor material and electrons in the case of an n-type semiconductor material, move through the material under the influence of an electric field. This parameter, which depends on the device architecture, can be measured using a field-effect device or space-charge limited current measurements.

Throughout the specification, structures may or may not be presented with chemical names. Where any question arises as to nomenclature, the structure prevails.

The present teachings provide various semiconducting small molecule compounds (small molecule semiconductors) as well as compositions and organic semiconductor materials prepared from such compounds and compositions. The organic semiconductor materials disclosed herein can exhibit useful electrical properties and can be solution-processable, e.g., spin-coatable and printable. The semiconductor materials disclosed herein can be used to fabricate various organic electronic articles, structures and devices, including field-effect transistors, light emitting transistors, unipolar circuitries, complementary circuitries, and photovoltaic devices.

More specifically, the present teachings relate to compounds having formula I:

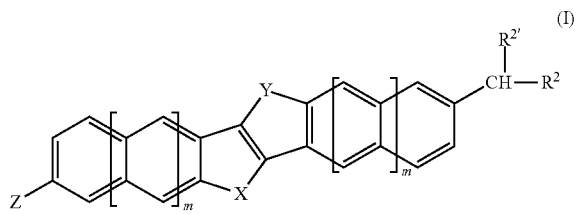
(I)

wherein:
X is selected from S, O, and CH=CH;
Y is selected from S, O, and CH=CH;
Z is H or $CHR^1R^{1'}$;
$R^1$, $R^{1'}$, $R^2$, and $R^{2'}$ independently are selected from a linear $C_{1-40}$ alkyl group, a linear $C_{2-40}$ alkenyl group, and a linear $C_{1-40}$ haloalkyl group; and
m, at each occurrence, independently is selected from 0, 1, 2, 3, and 4.

In some embodiments, the present compounds can be represented by formula II-IV:

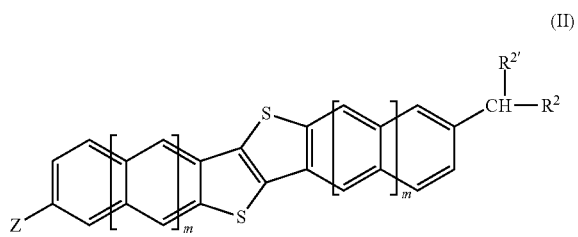
(II)

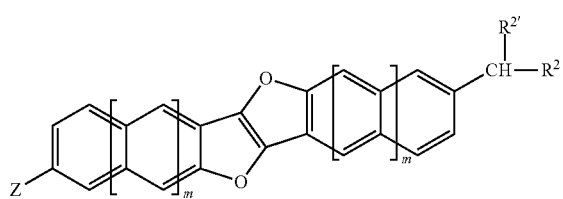
(III)

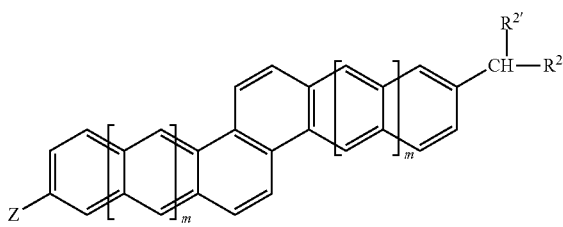
(IV)

wherein Z, $R^2$, $R^{2'}$, and m are as described herein. In certain embodiments, Z can be H. In other embodiments, Z can be $CHR^1R^{1'}$, in which case, $R^1$ can be the same or different from $R^{1'}$. Likewise, in some embodiments, $R^2$ can be different from $R^{2'}$. For example, $R^{1'}$ and $R^{2'}$ can be selected from a linear $C_{1-6}$ alkyl group, a linear $C_{2-6}$ alkenyl group, and a linear $C_{1-6}$ haloalkyl group; whereas $R^1$ and $R^2$ can be selected from a linear $C_{3-40}$ alkyl group, a linear $C_{3-40}$ alkenyl group, and a linear $C_{3-40}$ haloalkyl group; preferably selected from a linear $C_{6-40}$ alkyl group, a linear $C_{6-40}$ alkenyl group, and a linear $C_{6-40}$ haloalkyl group; more preferably selected from a linear $C_{8-40}$ alkyl group, a linear $C_{8-40}$ alkenyl group, and a linear $C_{8-40}$ haloalkyl group. In particular embodiments, $R^{1'}$ and $R^{2'}$ can be selected from $CH_3$, $CF_3$, $C_2H_5$, $CH_2CF_3$, $CF_2CH_3$, and $C_2F_5$; whereas $R^1$ and $R^2$ can be selected from a linear $C_{3-20}$ alkyl group, a linear $C_{3-20}$ alkenyl group, and a linear $C_{3-20}$ haloalkyl group.

In certain embodiments, the present compounds can be represented by formula IIa, IIIa, or IVa:

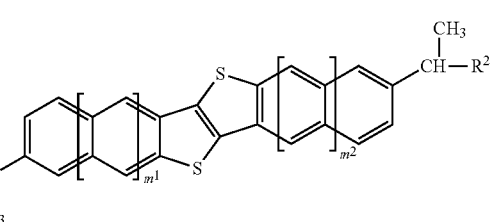
(IIa)

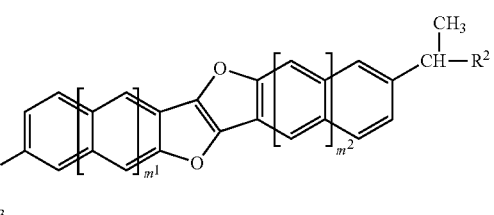
(IIIa)

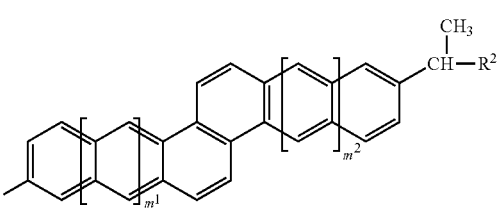
(IVa)

wherein $R^1$ and $R^2$ independently are selected from $C_2H_5$, n-$C_3H_7$, n-$C_4H_9$, n-$C_5H_{11}$, n-$C_6H_{13}$, n-$C_7H_{15}$, n-$C_8H_{17}$, n-$C_9H_{19}$, n-$C_{10}H_{21}$, n-$C_{11}H_{23}$, and n-$C_{12}H_{25}$; and $m^1$ and $m^2$ independently are selected from 0, 1, and 2. In particular embodiments, the present compounds can be optically pure stereoisomers. For example, certain compounds of formula II-IV can be stereospecific and can be represented by formula IIb, IIIb, IVb, IIc, IIIc, or IVc:

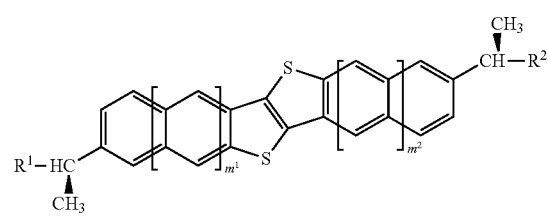
(IIb)

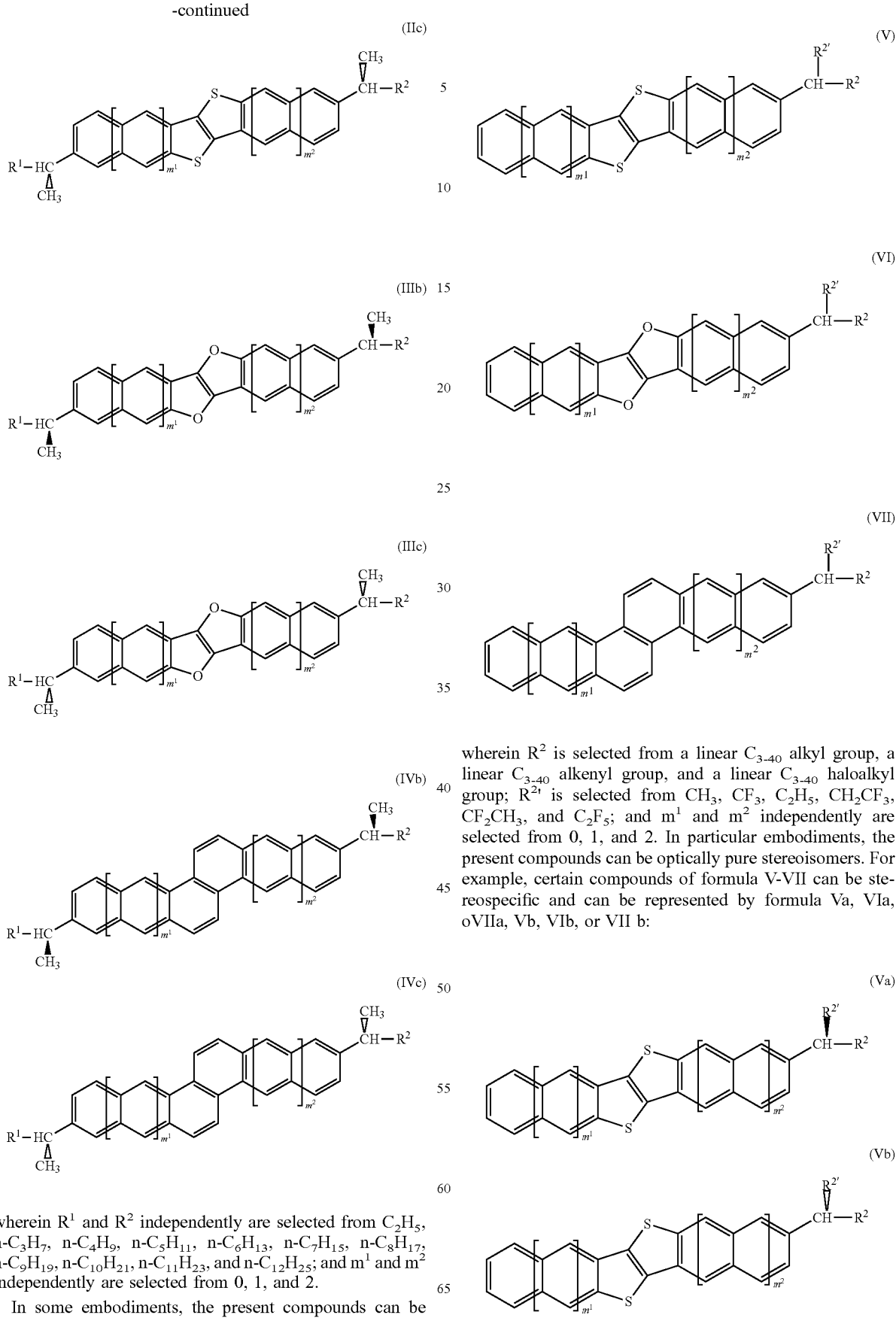

wherein $R^1$ and $R^2$ independently are selected from $C_2H_5$, n-$C_3H_7$, n-$C_4H_9$, n-$C_5H_{11}$, n-$C_6H_{13}$, n-$C_7H_{15}$, n-$C_8H_{17}$, n-$C_9H_{19}$, n-$C_{10}H_{21}$, n-$C_{11}H_{23}$, and n-$C_{12}H_{25}$; and $m^1$ and $m^2$ independently are selected from 0, 1, and 2.

In some embodiments, the present compounds can be represented by formula V, VI, or VII:

wherein $R^2$ is selected from a linear $C_{3-40}$ alkyl group, a linear $C_{3-40}$ alkenyl group, and a linear $C_{3-40}$ haloalkyl group; $R^{2'}$ is selected from $CH_3$, $CF_3$, $C_2H_5$, $CH_2CF_3$, $CF_2CH_3$, and $C_2F_5$; and $m^1$ and $m^2$ independently are selected from 0, 1, and 2. In particular embodiments, the present compounds can be optically pure stereoisomers. For example, certain compounds of formula V-VII can be stereospecific and can be represented by formula Va, VIa, oVIIa, Vb, VIb, or VII b:

-continued (VIa)
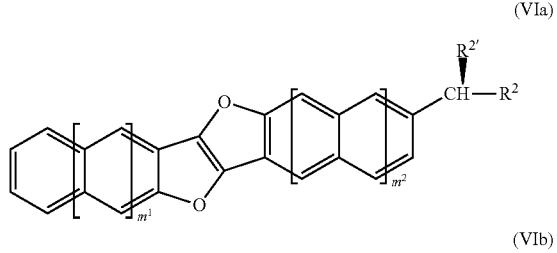

(VIb)
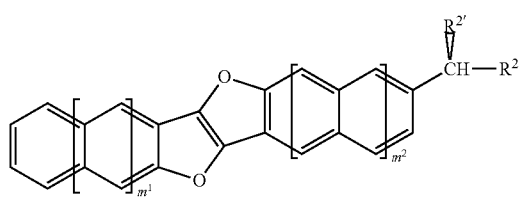

(VIIa)
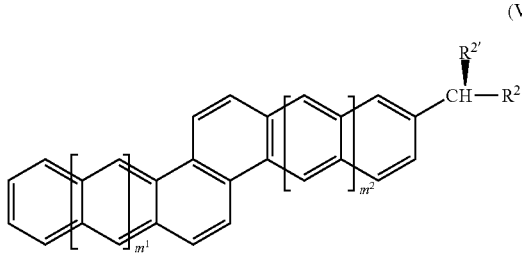

(VIIb)
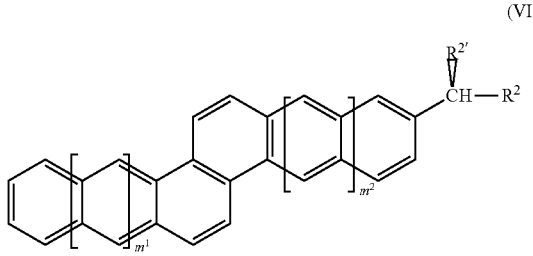

wherein $R^2$ is selected from a linear $C_{3\text{-}40}$ alkyl group, a linear $C_{3\text{-}40}$ alkenyl group, and a linear $C_{3\text{-}40}$ haloalkyl group; $R^{2'}$ is selected from $CH_3$, $CF_3$, $C_2H_5$, $CH_2CF_3$, $CF_2CH_3$, and $C_2F_5$; and $m^1$ and $m^2$ independently are selected from 0, 1, and 2.

In various embodiments of compounds of formula I, each m can be the same or different. For example, certain embodiments of the present compounds can be represented by formula:

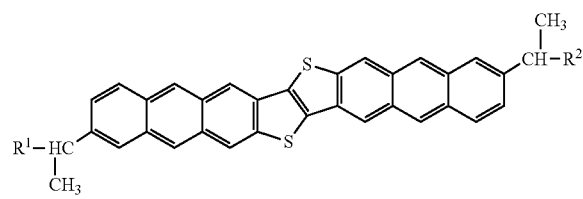

-continued

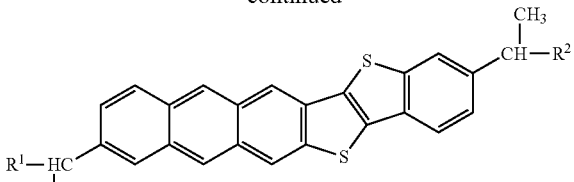

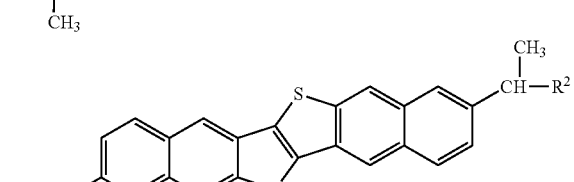

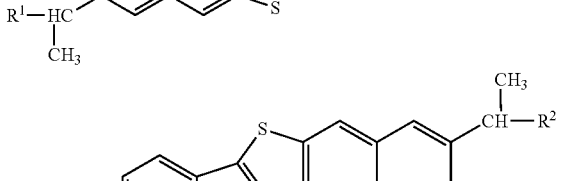

wherein $R^1$ and $R^2$ independently are selected from a linear $C_{3\text{-}40}$ alkyl group, a linear $C_{3\text{-}40}$ alkenyl group, and a linear $C_{3\text{-}40}$ haloalkyl group.

In certain embodiments of compounds of formula I, X and Y can be different. For example, certain compounds of formula I can be represented by formula:

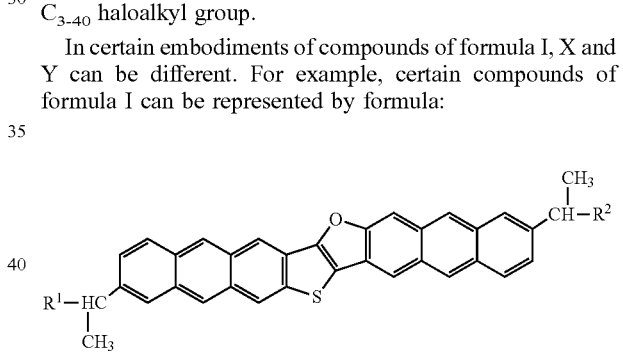

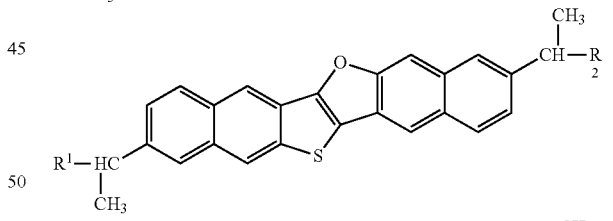

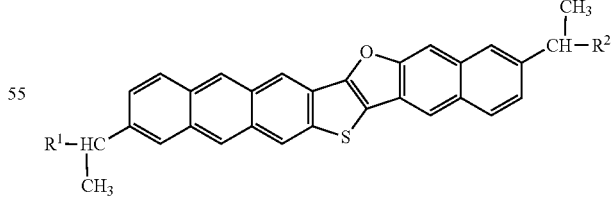

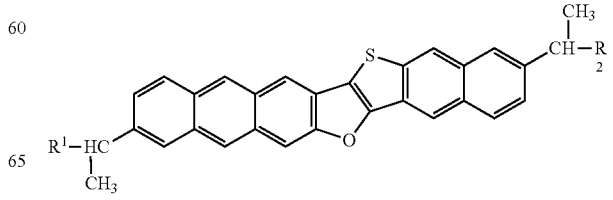

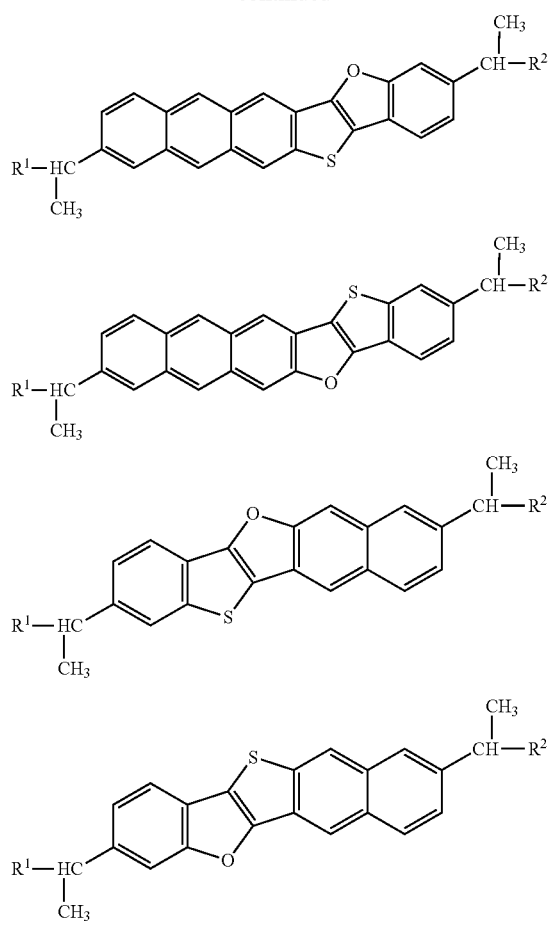
wherein $R^1$ and $R^2$ independently are selected from a linear $C_{3-40}$ alkyl group, a linear $C_{3-40}$ alkenyl group, and a linear $C_{3-40}$ haloalkyl group.
To further illustrate, certain compounds of formula I can be represented by formula:
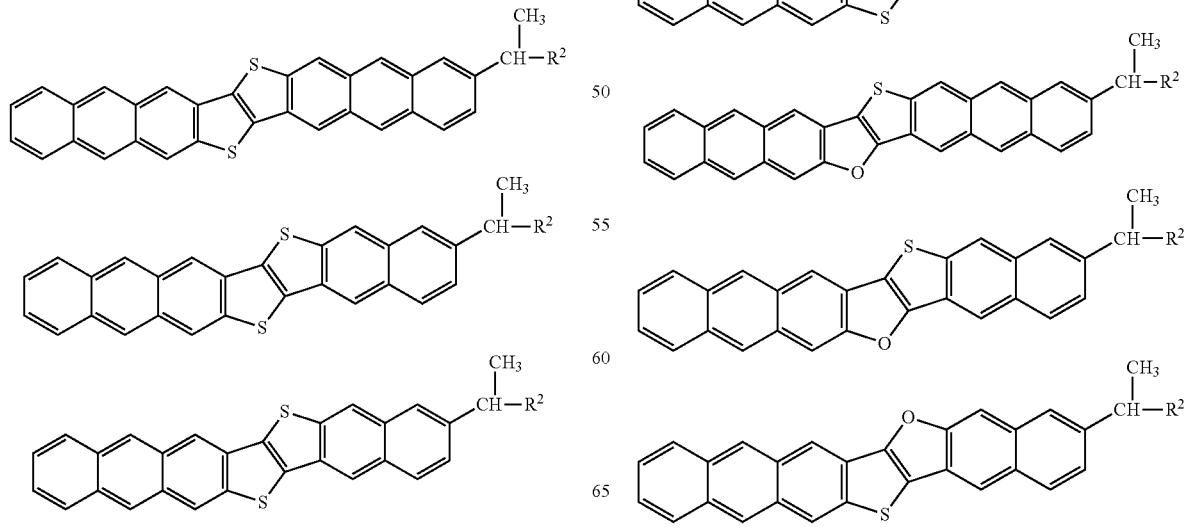
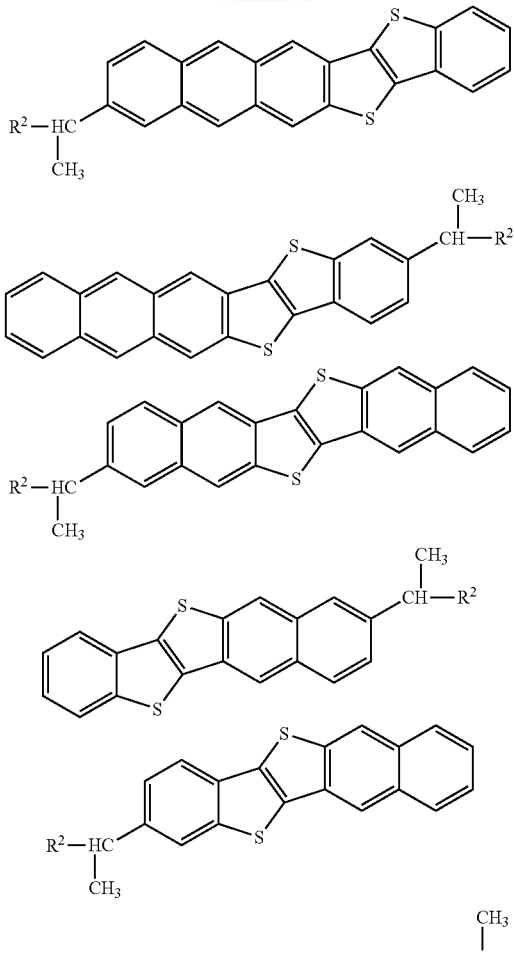

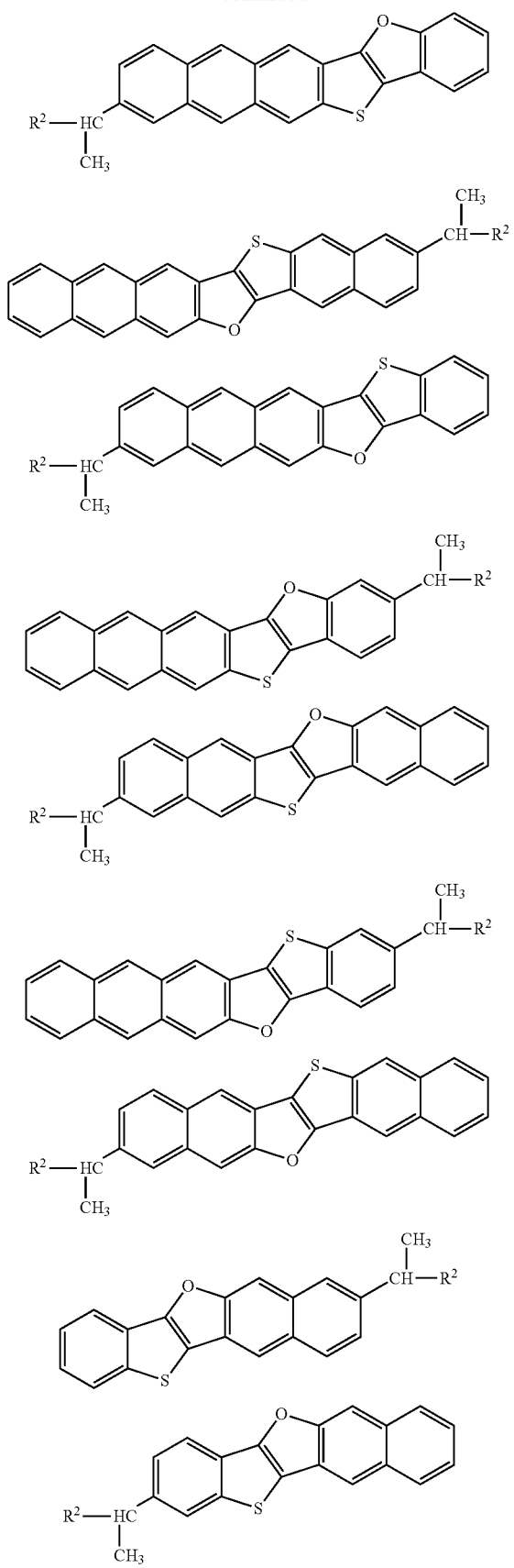

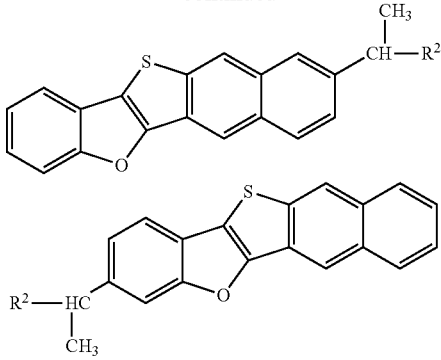

wherein $R^2$ is selected from a linear $C_{3-40}$ alkyl group, a linear $C_{3-40}$ alkenyl group, and a linear $C_{3-40}$ haloalkyl group.

Compounds of the present teachings can be prepared according to procedures described in Examples 1-5. Alternatively, the present compounds can be prepared from commercially available starting materials, compounds known in the literature, or via other readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the polymers described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), spectrophotometry (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Various compounds according to the present teachings can have good charge transport properties and can be stable under ambient conditions ("ambient stable"), soluble in common solvents, and in turn solution-processable into various articles, structures, or devices. In particular, compared to other compounds that may have a conjugated core similar to the present compounds, the substituent(s) $CHR^1R^{1'}$ and/or $CHR^2R^{2'}$ was found to confer greatly improved processability, specifically, in solution-phase at or near room temperature. For example, while prior art compounds may require hot solution processing (e.g., temperature at about 100° C.) with aggressive (e.g., chlorinated) solvents, the present compounds can be processed at a temperature less than about 50° C. using non-halogenated (e.g., non-chlorinated solvents).

Accordingly, the present teachings provide organic semiconductor devices that include one or more compounds described herein as semiconductors. Examples of such organic semiconductor devices include various electronic devices, optical devices, and optoelectronic devices such as thin film transistors (e.g., field effect transistors), photovoltaics, photodetectors, organic light emitting devices such as organic light emitting diodes (OLEDs) and organic light emitting transistors (OLETs), complementary metal oxide semiconductors (CMOSs), complementary inverters, diodes, capacitors, sensors, D flip-flops, rectifiers, ring oscillators, integrated circuits (ICs), radiofrequency identification (RFID) tags, electroluminescent displays, and organic memory devices. In some embodiments, the present teachings provide for a thin film semiconductor including one or more compounds described herein and a field effect transistor device including the thin film semiconductor. In particular, the field effect transistor device has a structure selected from top-gate bottom-contact structure, bottom-gate top-contact structure, top-gate top-contact structure, and bottom-gate bottom-contact structure. In certain embodiments, the field effect transistor device includes a dielectric material, wherein the dielectric material includes an organic dielectric material, an inorganic dielectric material, or a hybrid organic/inorganic dielectric material. In other embodiments, the present teachings provide for photovoltaic devices and organic light emitting devices incorporating a thin film semiconductor that includes one or more compounds described herein.

As described above, compounds of the present teachings generally have good solubility in a variety of common solvents. Thus, various embodiments of the present compounds can be processed via inexpensive solution-phase techniques into electronic devices, optical devices, or optoelectronic devices. As used herein, a compound can be considered soluble in a solvent when at least 1 mg of the compound can be dissolved in 1 mL of the solvent. Examples of common non-chlorinated organic solvents include petroleum ethers; acetonitrile; aromatic hydrocarbons such as benzene, toluene, xylene, and mesitylene; ketones such as acetone and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes; acetates such as methyl acetate, ethyl acetate, methyl formate, ethyl formate, isopropyl acetate, and butyl acetate; amides such as dimethylformamide and dimethylacetamide; sulfoxides such as dimethylsulfoxide; and cyclic solvents such as cyclopentanone, cyclohexanone, and 2-methypyrrolidone.

Accordingly, the present teachings further provide compositions that include one or more compounds disclosed herein dissolved or dispersed in a fluid medium, for example, an organic solvent. In some embodiments, the composition can further include one or more additives independently selected from detergents, dispersants, binding agents, compatiblizing agents, curing agents, initiators, humectants, antifoaming agents, wetting agents, pH modifiers, biocides, and bactereriostats. For example, surfactants and/or other polymers (e.g., polystyrene, polyethylene, poly-alpha-methyl styrene, polyisobutene, polypropylene, polymethylmethacrylate, and the like) can be included as a dispersant, a binding agent, a compatiblizing agent, and/or an antifoaming agent.

Various deposition techniques, including various solution-processing techniques, have been used with organic electronics. For example, much of the printed electronics technology has focused on inkjet printing, primarily because this technique offers greater control over feature position and multilayer registration. Inkjet printing is a noncontact process, which offers the benefits of not requiring a preformed master (compared to contact printing techniques), as well as digital control of ink ejection, thereby providing drop-on-demand printing. However, contact printing techniques have the key advantage of being well-suited for very fast roll-to-roll processing. Exemplary contact printing techniques include screen-printing, gravure, offset, flexo, and microcontact printing. Other solution processing techniques include, for example, spin coating, drop-casting, zone casting, dip coating, and blade coating.

The present compounds can exhibit versatility in their processing. Formulations including the present compounds can be printable via different types of printing techniques including gravure printing, flexographic printing, and inkjet printing, providing smooth and uniform films that allow, for example, the formation of a pinhole-free dielectric film thereon, and consequently, the fabrication of all-printed devices.

The present teachings, therefore, further provide methods of preparing a semiconductor material. The methods can include preparing a composition that includes one or more compounds disclosed herein dissolved or dispersed in a fluid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes one or more compounds disclosed herein. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying. In various embodiments, the depositing step can be carried out at low temperatures, for example, a temperature less than about 50° C., less than about 40° C., or about room temperature. More expensive processes such as vapor deposition also can be used.

The present teachings further provide articles of manufacture, for example, composites that include a thin film semiconductor of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), self-assembled superlattice/self-assembled nanodielectric (SAS/SAND) materials (e.g., as described in Yoon, M-H. et al., *PNAS*, 102 (13): 4678-4682 (2005), the entire disclosure of which is incorporated by reference herein), as well as hybrid organic/inorganic dielectric materials (e.g., as described in U.S. Pat. No. 7,678,463, the entire disclosure of which is incorporated by reference herein). In some embodiments, the dielectric component can include the crosslinked polymer blends described in U.S. Pat. No. 7,605,394, the entire disclosure of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Accordingly, an aspect of the present teachings relates to methods of fabricating an organic field effect transistor that incorporates a semiconductor material of the present teachings. The semiconductor materials of the present teachings can be used to fabricate various types of organic field effect transistors including top-gate top-contact structures, top-gate bottom-contact structures, bottom-gate top-contact structures, and bottom-gate bottom-contact structures.

FIG. 1 illustrates the four common types of OFET structures: (a) bottom-gate top-contact structure, (b) bottom-gate bottom-contact structure, (c) top-gate bottom-contact structure, and (d) top-gate top-contact structure. As shown, in each of the configurations, the semiconductor component is in contact with the source and drain electrodes, and the gate dielectric component is in contact with the semiconductor component on one side and the gate electrode on an opposite side.

In certain embodiments, OTFT devices can be fabricated with one or more compounds disclosed herein on doped silicon substrates, using $SiO_2$ as the dielectric, in top-contact geometries. In particular embodiments, the active semiconductor layer which incorporates one or more compounds disclosed herein can be deposited at room temperature or at an elevated temperature. In other embodiments, the active semiconductor layer which incorporates one or more compounds disclosed herein can be applied by spin-coating or printing as described herein. For top-contact devices, metallic contacts can be patterned on top of the films using shadow masks.

In certain embodiments, OTFT devices can be fabricated with one or more compounds disclosed herein on plastic foils, using polymers as the dielectric, in top-gate bottom-contact geometries. In particular embodiments, the active semiconducting layer which incorporates one or more compounds disclosed herein can be deposited at room temperature or at an elevated temperature. In other embodiments, the active semiconducting layer which incorporates one or more compounds disclosed herein can be applied by spin-coating or printing as described herein. Gate and source/drain contacts can be made of Au, other metals, or conducting polymers and deposited by vapor-deposition and/or printing.

In various embodiments, a semiconducting component incorporating one or more compounds disclosed herein can exhibit p-type semiconducting activity, for example, a hole mobility of $10^{-4}$ $cm^2$/V-sec or greater and/or a current on/off ratio ($I_{on}/I_{off}$) of $10^3$ or greater.

Other articles of manufacture in which one or more compounds disclosed herein can be useful include photovoltaics or solar cells. The present compounds can exhibit broad optical absorption and/or a tuned redox properties and bulk carrier mobilities. Accordingly, the present compounds can be used, for example, as a p-type semiconductor in a photovoltaic design, which includes an adjacent n-type semiconductor to form a p-n junction. The present compounds can be in the form of a thin film semiconductor, or a composite including the thin film semiconductor deposited on a substrate.

The present teachings further provide light emitting transistors including a source electrode, a drain electrode, a gate electrode, a dielectric material and a photoactive component comprising one or more compounds disclosed herein. In some embodiments, the compound(s) disclosed herein can be present in a blend material. In some embodiments, the photoactive component can be a laminate of two more layers, for example, including a light emitting layer and one or more organic charge transport layers. In particular embodiments, the present compound(s) can be present in one of the organic charge transport layers, particularly a hole transport layer.

The following examples are provided to illustrate further and to facilitate the understanding of the present teachings and are not in any way intended to limit the invention.

Unless otherwise noted, all reagents were purchased from commercial sources and used without further purification. Some reagents were synthesized according to known procedures. Anhydrous tetrahydrofuran (THF) was distilled from sodium/benzophenone. Reactions were carried out under nitrogen unless otherwise noted. UV-Vis spectra were recorded on a Cary Model 1 UV-vis spectrophotometer. NMR spectra were recorded on a Varian Unity Plus 500 spectrometer ($^1H$, 500 MHz; $^{13}C$, 125 MHz). Electrospray mass spectrometry was performed on a Thermo Finnegan model LCQ Advantage mass spectrometer.

EXAMPLE 1

Synthesis of 2,9-1MP-DNTT

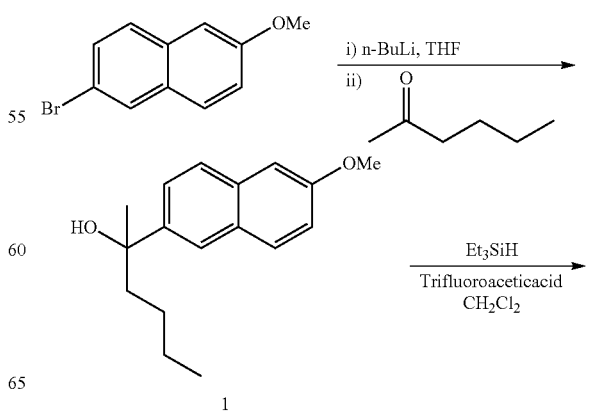

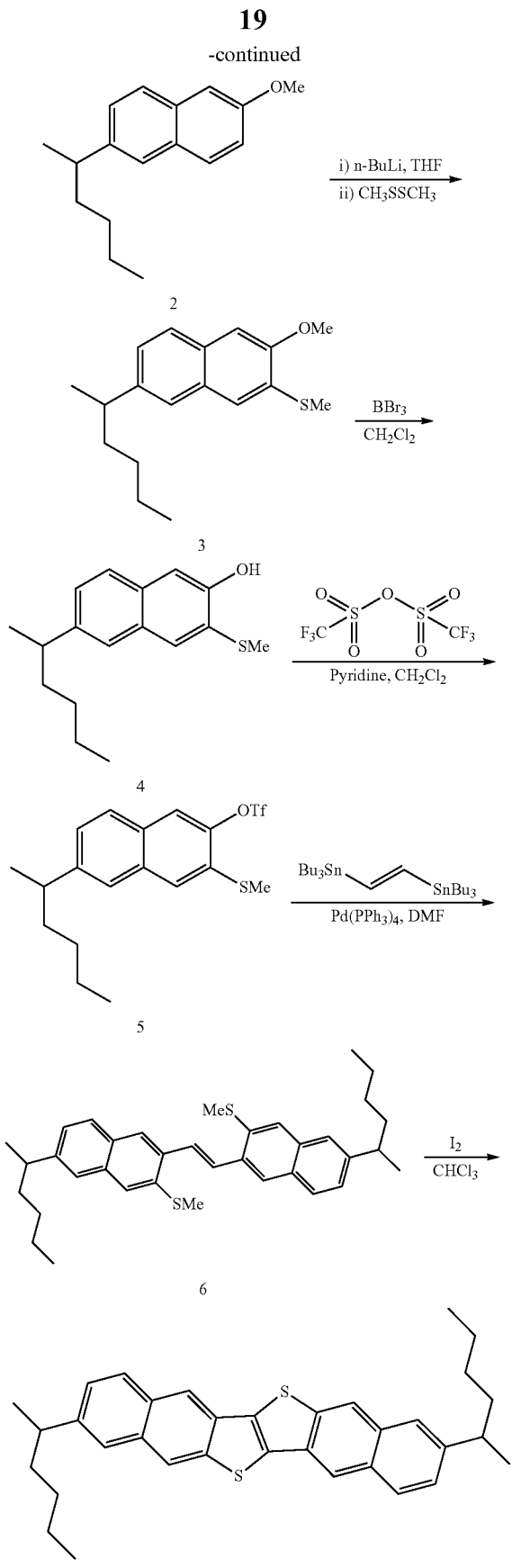

2-methoxy-6-(1-hydroxy-1-methylpentyl)naphthalene (1)

n-BuLi (2.5 M in hexanes, 6.2 mL, 15.5 mmol) was added dropwise to a solution of 2-methoxy-6-bromonaphthalene (3.5 g, 14.76 mmol) in THF (120 mL) at −78° C. under nitrogen. After stirring at −78° C. for 2 h, 2-hexanone (2.19 mL, 17.71 mmol) was added dropwise, and the solution was warmed to room temperature and stirred overnight. The reaction mixture was quenched with water and the organic layer was separated. Next, the organic phase was washed with water, dried over $Na_2SO_4$, and concentrated on a rotary evaporator to give a semi-solid crude compound. The crude was purified by column chromatography (silica gel, hexane:dichloromethane (1:4, v/v)) to give 1 as a white solid (3.0 g, 79% yield). $^1$H NMR (CDCl$_3$ 500 MHz): δ: 7.84 (d, 1H, J=1.5 Hz), 7.74 (d, 1H, J=8.5 Hz), 7.72 (d, 1H, J=8.5 Hz), 7.50 (dd, 1H, J=8.5 Hz, 1.5 Hz), 7.14 (m, 2H), 3.93 (s, 3H), 1.90 (m, 2H), 1.64 (s, 3H), 1.13-1.28 (m, 4H), 0.84 (t, 3H).

2-methoxy-6-(1-methylpentyl)naphthalene (2)

To a solution of 2-methoxy-6-(1-hydroxy-1-methylpentyl)naphthalene (1, 0.50 g, 1.935 mmol) in dichloromethane (15 mL) was added triethylsilane (0.35 mL, 2.19 mmol), and the solution was cooled to 0° C. under nitrogen. Then, the solution was treated with trifluoroacetic acid (1.49 mL, 19.34 mmol) dropwise over 30 min. The solution was warmed to room temperature and stirred for 3 h. The reaction mixture was carefully quenched with NaOH (1M, 25 mL) to give a basic mixture (pH~10), which was extracted with dichloromethane (100 mL). The organic phase was washed with water, dried over $Na_2SO_4$, concentrated on a rotary evaporator to give the crude compound as an oil. The crude product was purified by column chromatography (silica gel, hexane:dichloromethane (2:1, v/v)) to give 2 as a colorless oil (0.34 g, 73% yield). $^1$H NMR (CDCl$_3$ 500 MHz): δ: 7.70 (d, 1H, J=3.0 Hz), 7.68 (m, 1H), 7.54 (d, 1H, J=2.0 Hz), 7.31 (dd, 1H, 8.5 Hz, 2.0 Hz), 7.12 (m, 2H), 3.92 (s, 3H), 2.82 (m, 1H), 1.65 (m, 2H), 1.31 (d, 3H, J=7.0 Hz), 1.10-1.28 (m, 4H), 0.83 (t, 3H).

2-methoxy-3-methylthio-6-(1-methylpentyl)naphthalene (3)

To a solution of 2-methoxy-6-(1-methylpentyl)naphthalene (2, 1.37 g, 5.65 mmol) in THF (25 mL) was added dropwise n-butyllithium (2.5 M in hexanes, 2.49 mL, 6.22 mmol) at −78° C. under nitrogen. The solution was stirred at −78° C. for 15 min and at room temperature for another 1 h. The solution was then cooled to −78° C., and dimethyldisulfide (0.61 mL, 6.88 mmol) was added dropwise. The solution was warmed to room temperature and stirred for 15 h. The reaction mixture was quenched with saturated aqueous ammonium chloride solution (50 mL) and extracted with diethyl ether (200 mL). The organic phase was washed with brine, dried over $Na_2SO_4$, concentrated on a rotary evaporator to give the crude compound as a colorless oil. The crude product was purified by column chromatography (silica gel, hexane:dichloromethane (2:1, v/v)) to give 3 as a colorless oil (1.20 g, 74% yield). $^1$H NMR (CDCl$_3$ 500 MHz): δ: 7.64 (d, 1H, J=8.0 Hz), 7.49 (s, 1H), 7.43 (s, 1H), 7.25 (m, 1H), 7.07 (s, 1H), 4.00 (s, 3H), 2.80 (m, 1H), 2.55 (s, 3H), 1.63 (m, 2H), 1.31 (d, 3H, J=7.0 Hz), 1.15-1.23 (m, 4H), 0.84 (t, 3H).

6-(1-methylpentyl)-3-methylthio-2-naphthol (4)

A solution of BBr$_3$ in dichloromethane (1.0 M, 3.55 mL, 3.55 mmol) was added dropwise to a solution of 2-methoxy- 3-methylthio-6-(1-methylpentyl)naphthalene (3, 0.50 g, 1.73 mmol) in dichloromethane (5 mL) at −78° C. under nitrogen. The solution was then warmed to room temperature and stirred for 19 h. The reaction mixture was next poured into ice and the product was extracted with dichloromethane (50 mL). The organic phase was washed with brine, dried over $Na_2SO_4$, concentrated on a rotary evaporator to give 4 as a colorless oil, which was substantially pure and used for the next step without any further purification (0.44 g, 93% yield). $^1$H NMR (CDCl$_3$ 500 MHz): δ: 7.97 (s, 1H), 7.63 (d, J=8.5 Hz, 1H), 7.49 (brs, 1H), 7.31 (dd, J=8.5 Hz, 2.0 Hz, 1H), 7.30 (s, 1H), 6.59 (s, 1H), 2.81 (m, 1H), 2.43 (s, 3H), 1.65 (m, 2H), 1.31 (d, 3H, J=7.0 Hz), 1.16-1.29 (m, 4H), 0.85 (t, 3H).

6-(1-methylpentyl)-3-methylthio-2-naphtyl trifluoromethanesulfonate (5)

To a solution of 6-(1-methylpentyl)-3-methylthio-2-naphthol (4, 0.86 g, 3.13 mmol) and pyridine (0.81 mL, 10.02 mmol) in dichloromethane (20 mL) was added trifluoromethanesulfonic anhydride (0.61 mL, 3.63 mmol) at 0° C. under nitrogen. The reaction mixture was stirred at room temperature for 16 h, and then diluted with water (10 mL) and HCl (4M HCl, 10 mL). The organic phase was separated, washed with brine, dried over $Na_2SO_4$, concentrated on a rotary evaporator to give a crude oil product. The crude product was purified by column chromatography (silica gel, hexane:dichloromethane (9:1, v/v)) to give 5 as a colorless oil (1.10 g, 87% yield). $^1$H NMR (CDCl$_3$ 500 MHz): δ: 7.75 (d, 1H, J=8.5 Hz), 7.70 (s, 1H), 7.66 (s, 1H), 7.58 (br s, 1H), 7.38 (dd, 1H, J=8.5 Hz, 1.5 hHz), 2.85 (m, 1H), 2.60 (s, 3H), 1.67 (m, 2H), 1.32 (d, 3H, J=7.0 Hz), 1.15-1.28 (m, 4H), 0.85 (t, 3H).

trans-1,2-bis(6-(1-methylpentyl)-3-methylthionaphthalen-2-yl)ethene (6)

The reagents 6-(1-methylpentyl)-3-methylthio-2-naphtyl trifluoromethanesulfonate (5, 0.60 g, 1.48 mmol), trans-1,2-bis(tributylstannyl)ethene (0.45 g, 0.74 mmol), and Pd(PPh$_3$)$_4$ (25.6 mg, 0.022 mmol) were dissolved in dry DMF (20 mL) under nitrogen, and the reaction mixture was heated at 100° C. for 15 hours in dark. After cooling to room temperature, the reaction mixture was diluted with water and extracted with chloroform (100 mL). The organic phase was washed with brine, dried over $Na_2SO_4$, and concentrated on a rotary evaporator to give a semi-solid crude product. The crude product was purified by column chromatography (silica gel, hexane:dichloromethane (4:1, v/v)) to give 6 as a white solid (0.36 g, 82% yield). $^1$H NMR (CDCl$_3$ 500 MHz): δ: 8.07 (s, 2H), 7.79 (d, 2H, J=8.5 Hz), 7.65 (s, 2H), 7.62 (s, 2H), 7.53 (s, 2H), 7.30 (dd, 2H, J=8.5 Hz, 1.5 Hz), 2.84 (m, 2H), 2.60 (s, 6H), 1.68 (m, 4H), 1.33 (d, 6H, J=7.0 Hz), 1.17-1.31 (m, 8H), 0.86 (t, 6H).

2,9-Bis(1-methylpentyl)dinaphtho[2,3-b:2',3'-f]thieno[3,2-b]thiophene (2,9-1MP-DNTT)

A mixture of trans-1,2-bis(6-(1-methylpentyl)-3-methylthionaphthalen-2-yl)ethene (6, 0.80 g, 1.48 mmol) and iodine (12.01 g, 47.32 mmol) in chloroform (60 mL) was refluxed for 19 h. After cooling to room temperature, the reaction mixture was quenched with saturated aqueous sodium hydrogen sulfite solution (100 mL). The organic phase was separated, washed with brine, dried over $Na_2SO_4$, and concentrated on a rotary evaporator to yield a yellow crude solid. The crude was purified by column chromatography (silica gel, hexane:dichloromethane (4:1, v/v)) followed by recrystallization from hexane to yield 2,9-1MP-DNTT as a yellow crystalline solid (0.31 g, 41% yield). $^1$H NMR (CDCl$_3$ 500 MHz): δ: 8.36 (s, 2H), 8.32 (s, 2H), 7.97 (d, 2H, J=8.5 Hz), 7.70 (s, 2H), 7.41 (d, 2H, J=8.5 Hz), 2.90 (m, 2H), 1.70 (m, 4H), 1.36 (d, 6H, J=7.0 Hz), 1.12-1.34 (m, 8H), 0.89 (t, 6H). $^{13}$C NMR (CDCl$_3$): δ 14.12, 22.30, 22.85, 30.05, 37.98, 40.21, 119.75, 121.94, 124.38, 125.87, 128.26, 130.07, 131.67, 131.80, 133.36, 140.77, 145.56 ppm. Anal. calcd. for (C$_{34}$H$_{36}$S$_2$): C, 80.26; H, 7.13. Found: C, 80.33; H, 6.91. m.p. 262-263° C.

EXAMPLE 2

Synthesis of 2,9-1MB-DNTT

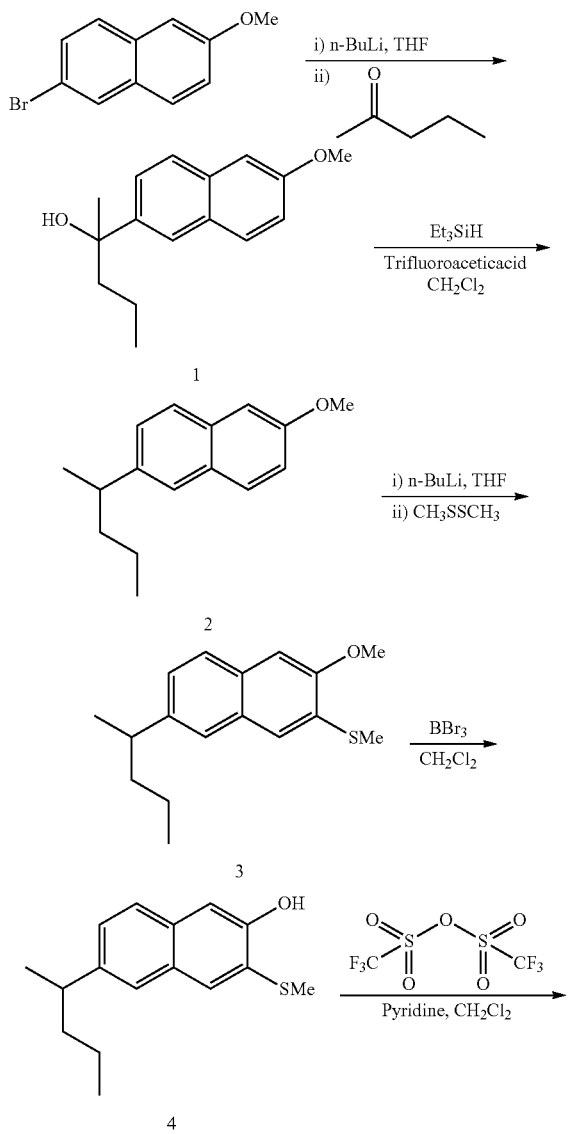

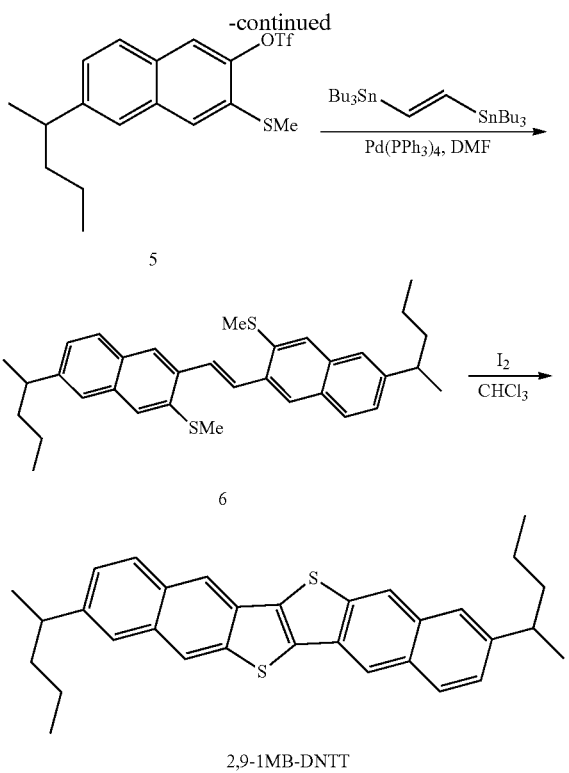

2,9-1MB-DNTT

2-methoxy-6-(1-hydroxy-1-methylbutyl)naphthalene (1)

n-BuLi (2.5 M in hexanes, 9.2 mL, 22.9 mmol) was added dropwise to a solution of 2-methoxy-6-bromonaphthalene (5.2 g, 21.85 mmol) in THF (100 mL) at −78° C. under nitrogen. After stirring at −78° C. for 1 h, 2-pentanone (2.79 mL, 26.22 mmol) was added dropwise, and the solution was warmed to room temperature and stirred overnight. The reaction mixture was quenched with water and the organic layer was separated. Next, the organic phase was washed with water, dried over $Na_2SO_4$, and concentrated on a rotary evaporator to give a semi-solid crude compound, which was used in the next step without any further purification (5.20 g, 97% yield). $^1$H NMR (CDCl$_3$ 500 MHz): δ: 7.83 (d, 1H, J=1.5 Hz), 7.75 (d, 1H, J=8.5 Hz), 7.72 (d, 1H, J=8.5 Hz), 7.52 (dd, 1H, J=8.5 Hz, 1.5 Hz), 7.12 (m, 2H), 3.93 (s, 3H), 1.91 (m, 2H), 1.64 (s, 3H), 1.14-1.29 (m, 2H), 0.83 (t, 3H).

2-methoxy-6-(1-methylbutyl)naphthalene (2)

To a solution of 2-methoxy-6-(1-hydroxy-1-methylbutyl)naphthalene (1, 5.34 g, 21.86 mmol) in dichloromethane (120 mL) was added triethylsilane (3.90 mL, 24.70 mmol), and the solution was cooled to 0° C. under nitrogen. Then, the solution was treated with trifluoroacetic acid (16.84 mL, 218.6 mmol) dropwise over 30 min. The solution was warmed to room temperature and stirred overnight. The reaction mixture was carefully quenched with NaOH (1M, 25 mL) to give a basic mixture (pH~10), which was extracted with dichloromethane (100 mL). The organic phase was washed with water, dried over $Na_2SO_4$, concentrated on a rotary evaporator to give the crude compound as an oil. The crude product was purified by column chromatography (silica gel, hexane:dichloromethane (2:1, v/v)) to give 2 as a colorless oil (3.20 g, 64% yield). $^1$H NMR (CDCl$_3$ 500 MHz): δ: 7.71 (d, 1H, J=3.0 Hz), 7.69 (m, 1H), 7.54 (d, 1H, J=2.0 Hz), 7.34 (dd, 1H, 8.5 Hz, 2.0 Hz), 7.14 (m, 2H), 3.93 (s, 3H), 2.83 (m, 1H), 1.63 (m, 2H), 1.31 (d, 3H, J=7.0 Hz), 1.11-1.29 (m, 2H), 0.82 (t, 3H).

2-methoxy-3-methylthio-6-(1-methylbutyl)naphthalene (3)

To a solution of 2-methoxy-6-(1-methylbutyl)naphthalene (2, 3.00 g, 13.14 mmol) in THF (60 mL) was added dropwise n-butyllithium (2.5 M in hexanes, 5.78 mL, 14.45 mmol) at −78° C. under nitrogen. The solution was stirred at −78° C. for 15 min and at room temperature for another 1 h. The solution was then cooled to −78° C., and dimethyldisulfide (1.40 mL, 15.77 mmol) was added dropwise. The solution was warmed to room temperature and stirred overnight. The reaction mixture was quenched with saturated aqueous ammonium chloride solution (50 mL) and extracted with diethyl ether (200 mL). The organic phase was washed with brine, dried over $Na_2SO_4$, concentrated on a rotary evaporator to give the crude compound as a colorless oil. The crude product was purified by column chromatography (silica gel, hexane:dichloromethane (3:1, v/v)) to give 3 as a colorless oil (2.60 g, 72% yield). $^1$H NMR (CDCl$_3$ 500 MHz): δ: 7.63 (d, 1H, J=8.0 Hz), 7.52 (s, 1H), 7.44 (s, 1H), 7.24 (m, 1H), 7.08 (s, 1H), 4.01 (s, 3H), 2.83 (m, 1H), 2.54 (s, 3H), 1.63 (m, 2H), 1.31 (d, 3H, J=7.0 Hz), 1.16-1.24 (m, 2H), 0.83 (t, 3H).

6-(1-methylbutyl)-3-methylthio-2-naphthol (4)

A solution of BBr$_3$ in dichloromethane (1.0 M, 18.67 mL, 18.67 mmol) was added dropwise to a solution of 2-methoxy-3-methylthio-6-(1-methylpentyl)naphthalene (3, 2.50 g, 9.11 mmol) in dichloromethane (25 mL) at −78° C. under nitrogen. The solution was then warmed to room temperature and stirred for 20 h. The reaction mixture was next poured into ice and the product was extracted with dichloromethane (50 mL). The organic phase was washed with brine, dried over $Na_2SO_4$, concentrated on a rotary evaporator to give 4 as a colorless oil, which was substantially pure and used for the next step without any further purification (2.35 g, 99% yield). $^1$H NMR (CDCl$_3$ 500 MHz): δ: 7.98 (s, 1H), 7.64 (d, J=8.5 Hz, 1H), 7.49 (brs, 1H), 7.33 (dd, J=8.5 Hz, 2.0 Hz, 1H), 7.31 (s, 1H), 6.60 (s, 1H), 2.82 (m, 1H), 2.45 (s, 3H), 1.64 (m, 2H), 1.32 (d, 3H, J=7.0 Hz), 1.17-1.30 (m, 2H), 0.83 (t, 3H).

6-(1-methylbutyl)-3-methylthio-2-naphtyl trifluoromethanesulfonate (5)

To a solution of 6-(1-methylbutyl)-3-methylthio-2-naphthol (4, 2.0 g, 7.68 mmol) and pyridine (1.99 mL, 24.58 mmol) in dichloromethane (50 mL) was added trifluoromethanesulfonic anhydride (1.48 mL, 8.83 mmol) at 0° C. under nitrogen. The reaction mixture was stirred at room temperature for 16 h, and then diluted with water (10 mL) and HCl (4M HCl, 10 mL). The organic phase was separated, washed with brine, dried over $Na_2SO_4$, concentrated on a rotary evaporator to give a crude oil product. The crude product was purified by column chromatography (silica gel, hexane:dichloromethane (8:1, v/v)) to give 5 as a colorless oil (2.40 g, 80% yield). $^1$H NMR (CDCl$_3$ 500 MHz): δ: 7.74 (d, 1H, J=8.5 Hz), 7.71 (s, 1H), 7.67 (s, 1H), 7.60 (br s, 1H), 7.39 (dd, 1H, J=8.5 Hz, 1.5 hHz), 2.83 (m, 1H), 2.59 (s, 3H), 1.68 (m, 2H), 1.32 (d, 3H, J=7.0 Hz), 1.15-1.28 (m, 2H), 0.83 (t, 3H).

trans-1,2-bis(6-(1-methylbutyl)-3-methylthionaphthalen-2-yl)ethene (6)

The reagents 6-(1-methylbutyl)-3-methylthio-2-naphtyl trifluoromethanesulfonate (5, 1.50 g, 3.82 mmol), trans-1,2-bis(tributylstannyl)ethene (1.16 g, 1.91 mmol), and Pd(PPh$_3$)$_4$ (66.2 mg, 0.057 mmol) were dissolved in dry DMF (50 mL) under nitrogen, and the reaction mixture was heated at 100° C. for 18 hours in dark. After cooling to room temperature, the reaction mixture was diluted with water and extracted with chloroform (100 mL). The organic phase was washed with brine, dried over Na$_2$SO$_4$, and concentrated on a rotary evaporator to give a semi-solid crude product. The crude product was purified by column chromatography (silica gel, hexane:dichloromethane (4:1, v/v)) to give 6 as a white solid (0.83 g, 85% yield). $^1$H NMR (CDCl$_3$ 500 MHz): δ: 8.10 (s, 2H), 7.80 (d, 2H, J=8.5 Hz), 7.67 (s, 2H), 7.63 (s, 2H), 7.54 (s, 2H), 7.31 (dd, 2H, J=8.5 Hz, 1.5 Hz), 2.83 (m, 2H), 2.61 (s, 6H), 1.69 (m, 4H), 1.34 (d, 6H, J=7.0 Hz), 1.18-1.32 (m, 4H), 0.85 (t, 6H).

2,9-Bis(1-methylbutyl)dinaphtho [2,3-b:2',3'-f]thieno[3,2-b]thiophene (2,9-1MB-DNTT)

A mixture of trans-1,2-bis(6-(1-methylbutyl)-3-methylthionaphthalen-2-yl)ethene (6, 0.60 g, 1.17 mmol) and iodine (9.5 g, 37.44 mmol) in chloroform (40 mL) was refluxed for 19 h. After cooling to room temperature, the reaction mixture was quenched with saturated aqueous sodium hydrogen sulfite solution (100 mL). The organic phase was separated, washed with brine, dried over Na$_2$SO$_4$, and concentrated on a rotary evaporator to yield a yellow crude solid. The crude was purified by column chromatography (silica gel, hexane:chloroform (4:1, v/v)) followed by recrystallization from hexane to yield 2,9-1MB-DNTT as a yellow crystalline solid (0.31 g, 40% yield). $^1$H NMR (CDCl$_3$ 500 MHz): δ: 8.35 (s, 2H), 8.32 (s, 2H), 7.97 (d, 2H, J=8.5 Hz), 7.70 (s, 2H), 7.41 (d, 2H, J=8.5 Hz), 2.93 (m, 2H), 1.74 (m, 4H), 1.37 (d, 6H, J=7.0 Hz), 1.13-1.35 (m, 4H), 0.91 (t, 6H). $^{13}$C NMR (CDCl$_3$): δ 14.23, 20.93, 22.25, 39.94, 40.50, 119.75, 121.93, 124.38, 125.87, 128.26, 130.06, 131.66, 131.79, 133.36, 140.78, 145.51 ppm. Anal. calcd. for (C$_{32}$H$_{32}$S$_2$): C, 79.95; H, 6.71. Found: C, 80.03; H, 6.77. m.p. 280-281° C.

EXAMPLE 3

Synthesis of 2,9-1MD-DNTT

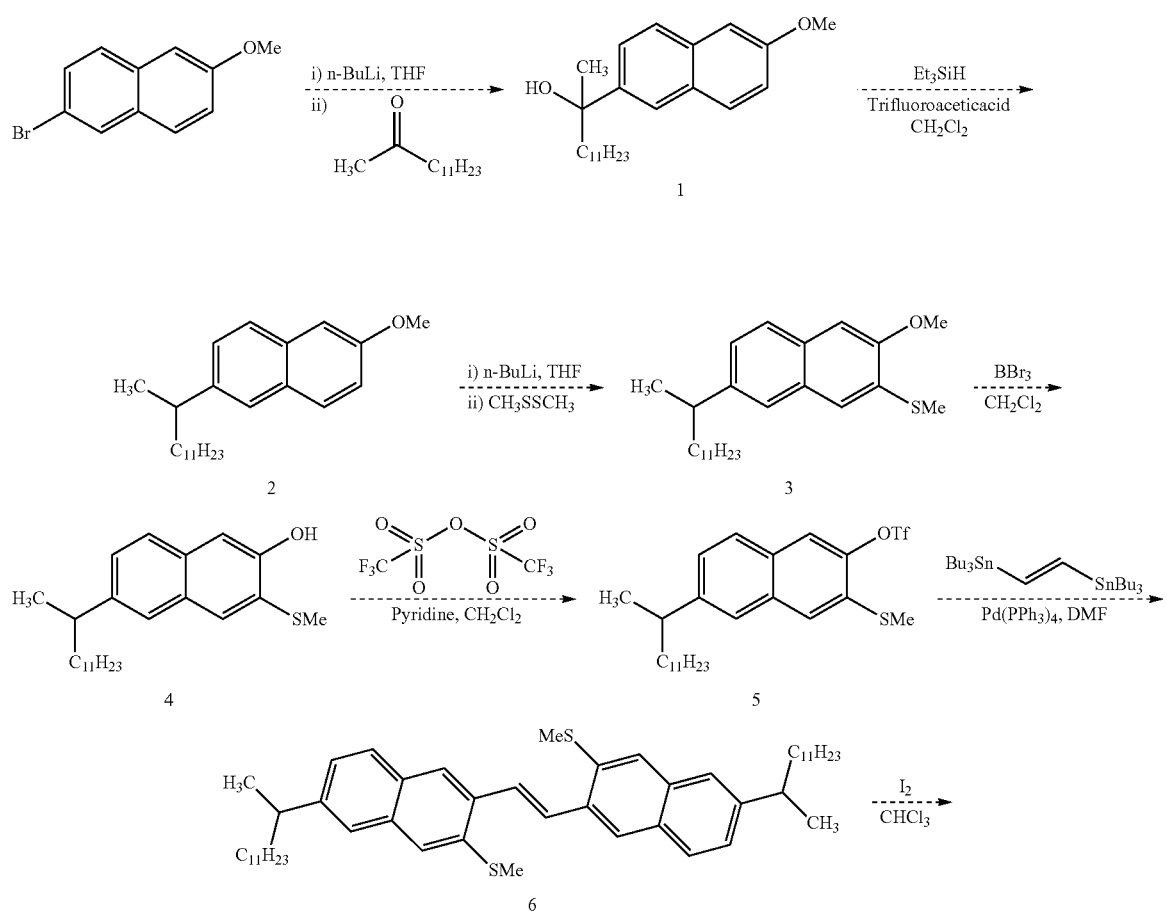

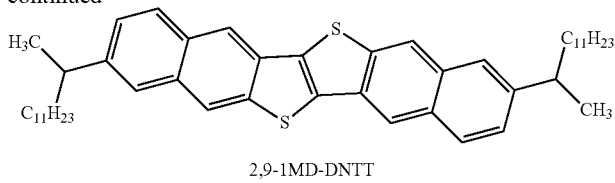

2,9-1MD-DNTT

In this example, 2,9-1MD-DNTT (Example X) has longer alkyl substitutent (R=—CH(CH$_3$)C$_{11}$H$_{23}$) compared to those of Examples 1 (2,9-1MP-DNTT, R=—CH(CH$_3$)C$_4$H$_9$) and 2 (2,9-1MB-DNTT, R=—CH(CH$_3$)C$_3$H$_7$). Longer alkyl chains are expected to enhance molecular ordering in thin-film phase via alkyl chain interdigitations, which may result in highly crystalline, continuous and uniform film morphologies with enhanced charge transport characteristics. Additionally, longer alkyl chain also ensures good solubility of the semiconductor in common organic solvents for efficient solution-processing. The effect of alkyl chain length on charge transporting characteristics of non-soluble DNTT semiconductors was demonstrated in *Adv. Mater.* 2011, 23, 1222-1225, and ~5-10-fold mobility enhancement was observed going from -n-C$_6$H$_{13}$ to -n-C$_{12}$H$_{13}$ for vapor-deposited OTFTs.

EXAMPLE 4

Synthesis of 2-1MP-DNTT

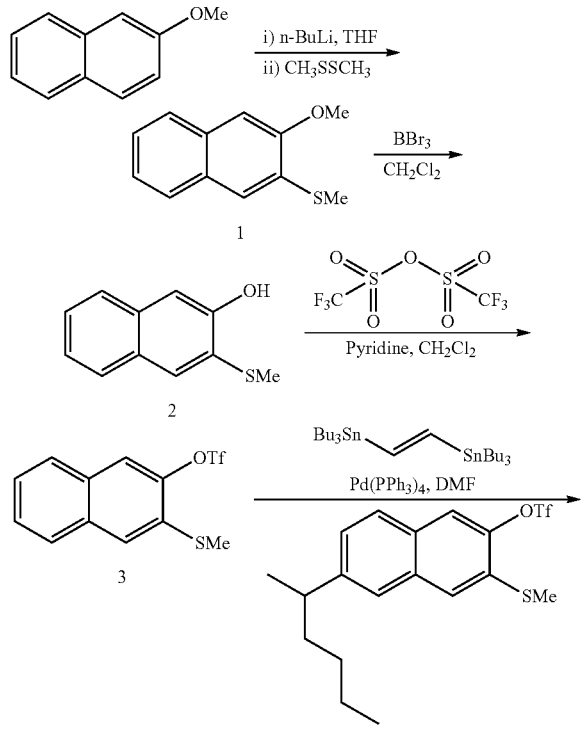

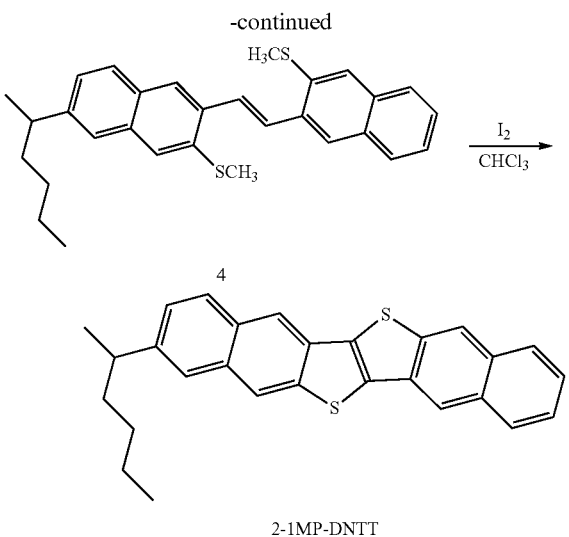

2-1MP-DNTT 2-methoxy-3-methylthionaphthalene (1)

To a solution of 2-methoxynaphthalene (5.00 g, 31.60 mmol) in THF (30 mL) was added dropwise n-butyllithium (2.5 M in hexanes, 13.91 mL, 34.77 mmol) at −78° C. under nitrogen. The solution was stirred at −78° C. for 15 min and at room temperature for another 1 h. The solution was then cooled to −78° C., and dimethyldisulfide (3.36 mL, 37.88 mmol) was added dropwise. The solution was warmed to room temperature and stirred for 15 h. The reaction mixture was quenched with saturated aqueous ammonium chloride solution (50 mL) and extracted with diethyl ether (200 mL). The organic phase was washed with brine, dried over Na$_2$SO$_4$, concentrated on a rotary evaporator to give the crude compound as a white solid. The crude product was purified by recrystallization from Hexanes to give 1 as a white solid (4.64 g, 71% yield). $^1$H NMR (CDCl$_3$ 500 MHz): δ: 7.71 (d, 2H, J=9.0 Hz), 7.42 (s, 1H), 7.38 (m, 2H), 7.10 (s, 1H), 4.02 (s, 3H), 2.56 (s, 3H).

3-methylthio-2-naphthol (2)

A solution of BBr$_3$ in dichloromethane (1.0 M, 37.10 mL, 37.10 mmol) was added dropwise to a solution of 2-methoxy-3-methylthionaphthalene (1, 3.70 g, 18.11 mmol) in dichloromethane (10 mL) at −78° C. under nitrogen. The solution was then warmed to room temperature and stirred for 16 h. The reaction mixture was next poured into ice and the product was extracted with dichloromethane (50 mL). The organic phase was washed with brine, dried over Na$_2$SO$_4$, concentrated on a rotary evaporator to give 2 as a white solid, which was practically pure and used for the next step without any further purification (2.70 g, 78% yield). 1H NMR (CDCl₃ 500 MHz): δ: 7.98 (s, 1H), 7.72 (m, 1H), 7.65 (m, 1H), 7.41 (m, 1H), 7.33 (s, 1H), 7.30 (m, 1H), 6.62 (s, 1H), 2.42 (s, 3H).

3-methylthio-2-naphtyl trifluoromethanesulfonate (3)

To a solution of 3-methylthio-2-naphthol (2, 3.0 g, 15.77 mmol) and pyridine (4.08 mL, 50.45 mmol) in dichloromethane (40 mL) was added trifluoromethanesulfonic anhydride (3.05 mL, 18.16 mmol) at 0° C. under nitrogen. The reaction mixture was stirred at room temperature for 18 h, and then diluted with water (30 mL) and HCl (4M HCl, 30 mL). The organic phase was separated, washed with brine, dried over Na₂SO₄, concentrated on a rotary evaporator to give a crude oil product. The crude product was purified by column chromatography (Silica gel, Hexane:Dichloromethane (5:1, v/v)) to give 3 as a white solid (3.50 g, 69% yield). ¹H NMR (CDCl₃ 500 MHz): δ: 7.81 (m, 2H), 7.74 (s, 1H), 7.70 (s, 1H), 7.54 (m, 2H), 2.61 (s, 3H).

trans-1-(6-(1-methylpentyl)-3-methylthionaphthalen-2-yl)-2-(3-methylthionaphthalen-2-yl)ethene (4)

The reagents 3-methylthio-2-naphtyl trifluoromethanesulfonate (3, 0.265 g, 0.825 mmol), 6-(1-methylpentyl)-3-methylthio-2-naphtyl trifluoromethanesulfonate (0.335 g, 0.825 mmol), trans-1,2-bis(tributylstannyl)ethene (0.500 g, 0.825 mmol), and Pd(PPh₃)₄ (28.6 mg, 0.025 mmol) were dissolved in dry DMF (20 mL) under nitrogen, and the reaction mixture was heated at 100° C. for 18 hours in dark. After cooling to room temperature, the reaction mixture was diluted with water and extracted with chloroform (200 mL). The organic phase was washed with brine, dried over Na₂SO₄, and concentrated on a rotary evaporator to give a semi-solid crude product. The crude product was purified by column chromatography (Silica gel, Hexane:Dichloromethane (2:1, v/v)) to give 4 as a yellow semisolid (0.14 g, 37% yield). ¹H NMR (CDCl₃ 500 MHz): δ: 8.11 (s, 1H), 8.07 (s, 1H), 7.78 (d, 1H, J=7.0 Hz), 7.79 (d, 1H, J=8.5 Hz), 7.77 (d, 1H, J=7.5 Hz), 7.66 (m, 3H), 7.62 (s, 1H), 7.53 (s, 1H), 7.45 (m, 2H), 7.31 (dd, 1H, J=8.5 Hz, 1.5 Hz), 2.85 (m, 1H), 2.61 (s, 3H), 2.60 (s, 3H), 1.67 (m, 2H), 1.33 (d, 3H, J=7.0 Hz), 1.17-1.31 (m, 4H), 0.87 (t, 3H).

2-(1-methylpentyl)dinaphtho[2,3-b:2',3'-f]thieno[3,2-b]thiophene (2-1MP-DNTT)

A mixture of trans-1-(6-(1-methylpentyl)-3-methylthionaphthalen-2-yl)-2-(3-methylthionaphthalen-2-yl)ethene (4, 0.130 g, 0.285 mmol) and iodine (2.31 g, 9.11 mmol) in chloroform (10 mL) was refluxed for 23 h. After cooling to room temperature, the reaction mixture was quenched with saturated aqueous sodium hydrogen sulfite solution (30 mL). The organic phase was separated, washed with brine, dried over Na₂SO₄, and concentrated on a rotary evaporator to yield a yellow crude solid. The crude was purified by passing through a short plug of silica gel (chloroform as the eluent) followed by a recrystallization from chloroform to yield 2-1MP-DNTT as a yellow solid (20 mg, 16.5% yield). ¹H NMR (CDCl₃ 500 MHz): δ: 8.43 (s, 1H), 8.37 (s, 2H), 8.34 (s, 1H), 8.05 (m, 1H), 7.97 (m, 2H), 7.70 (s, 1H), 7.54 (m, 2H), 7.42 (dd, 1H, J=8.5 Hz, 1.5 Hz), 2.91 (m, 1H), 1.71 (m, 2H), 1.37 (d, 3H, J=7.0 Hz), 1.11-1.35 (m, 4H), 0.87 (t, 3H). m.p. >300° C.

EXAMPLE 5

Synthesis of 1MP-NTTB

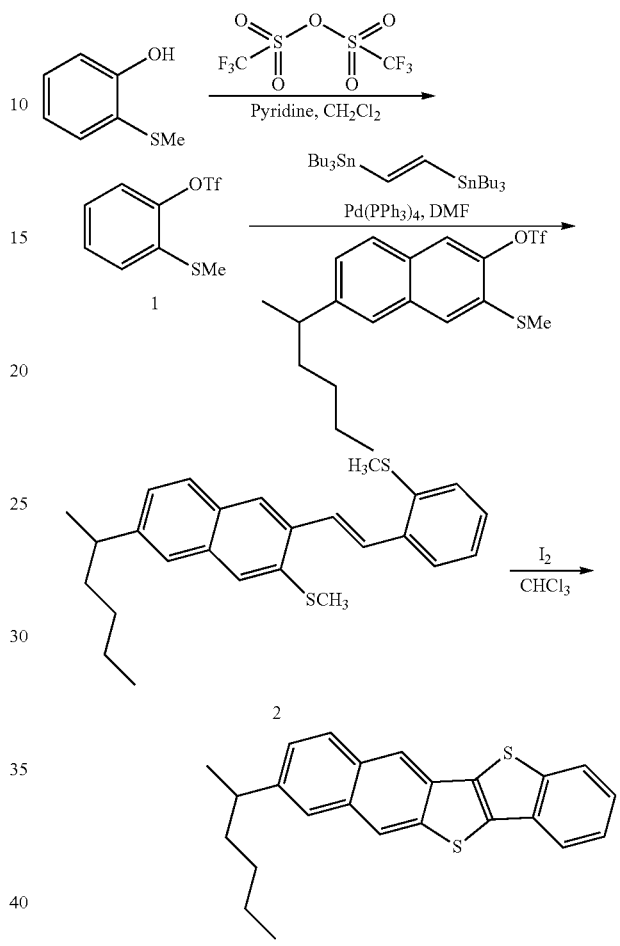

2-(methylthio)phenyl trifluoromethanesulfonate (1)

To a solution of 2-(methylthio)phenol (5.0 g, 35.6 mmol) and pyridine (9.22 mL, 114.1 mmol) in dichloromethane (40 mL) was added trifluoromethanesulfonic anhydride (6.88 mL, 41.0 mmol) at 0° C. under nitrogen. The reaction mixture was stirred at room temperature for 18 h, and then diluted with water (40 mL) and HCl (4M HCl, 40 mL). The organic phase was separated, washed with brine, dried over Na₂SO₄, concentrated on a rotary evaporator to give a crude oil product. The crude product was purified by column chromatography (Silica gel, Hexane:Dichloromethane (4:1, v/v)) to give 1 as a colorless oil (9.40 g, 96% yield). ¹H NMR (CDCl₃ 500 MHz): δ: 7.36 (dd, 2H, J=4.5 Hz, 1.5 Hz), 7.25 (m, 2H), 2.51 (s, 3H). trans-1-(6-(1-methylpentyl)-3-methylthionaphthalen-2-yl)-2-(2-(methylthio)phenyl)ethene (2): The reagents 2-(methylthio)phenyl trifluoromethanesulfonate (1, 1.00 g, 3.69 mmol), 6-(1-methylpentyl)-3-methylthio-2-naphtyl trifluoromethanesulfonate (1.50 g, 3.69 mmol), trans-1,2-bis(tributylstannyl)ethene (2.24 g, 3.69 mmol), and Pd(PPh₃)₄ (128 mg, 0.11 mmol) were dissolved in dry DMF (90 mL) under nitrogen, and the reaction mixture was heated at 100° C. for 14 hours in dark. After cooling to room temperature, the reaction mixture was diluted with water and extracted with chloroform (300 mL). The organic phase was washed with brine, dried over $Na_2SO_4$, and concentrated on a rotary evaporator to give a semi-solid crude product. The crude product was purified by column chromatography (Silica gel, Hexane:Dichloromethane (5:1, v/v)) to give 2 as a yellow semisolid (0.365 g, 24% yield). $^1$H NMR ($CDCl_3$ 500 MHz): δ: 8.03 (s, 1H), 7.77 (d, 1H, J=8.0 Hz), 7.69 (dd, 1H, J=8.0 Hz, 1.5 Hz), 7.60 (s, 1H), 7.58 (s, 1H), 7.57 (s, 1H), 7.52 (s, 1H), 7.31 (m, 4H), 2.82 (m, 1H), 2.58 (s, 3H), 2.50 (s, 3H), 1.66 (m, 2H), 1.33 (d, 3H, J=7.0 Hz), 1.17-1.31 (m, 4H), 0.85 (t, 3H).

2-(1-methylpentyl)naphtho[2,3-b]benzo[1,2-f]thieno[3,2-b]thiophene (1MP-NTTB)

A mixture of trans-1-(6-(1-methylpentyl)-3-methylthionaphthalen-2-yl)-2-(2-(methylthio)phenyl)ethane (2, 0.365 g, 0.90 mmol) and iodine (7.29 g, 28.72 mmol) in chloroform (30 mL) was refluxed for 16 h. After cooling to room temperature, the reaction mixture was quenched with saturated aqueous sodium hydrogen sulfite solution (60 mL). The organic phase was separated, washed with brine, dried over $Na_2SO_4$, and concentrated on a rotary evaporator to yield a yellow crude solid. The crude was purified by passing through a short plug of silica gel (chloroform as the eluent) followed by a recrystallization from chloroform to yield 1MP-NTTB as a yellow solid (120 mg, 36% yield). $^1$H NMR ($CDCl_3$ 500 MHz): δ: 8.34 (s, 1H), 8.33 (s, 1H), 7.97 (m, 2H), 7.89 (d, 1H, J=8.0 Hz), 7.69 (s, 1H), 7.50 (m, 1H), 7.44 (m, 2H), 2.90 (m, 1H), 1.70 (m, 2H), 1.36 (d, 3H, J=7.0 Hz), 1.12-1.37 (m, 4H), 0.85 (t, 3H). MS (MALDI) m/z ($M^+$.): calc. for ($C_{24}H_{22}S_2$), 374.56. found, 373.86. Anal. calcd. for ($C_{24}H_{22}S_2$): C, 76.96; H, 5.92. Found: C, 76.88; H, 5.90. m.p. >210-211° C.

EXAMPLE 6

Solubility Data Comparison Between 2,9-$C_n$-DNTT (n=6, 8, 10, 12) and 2,9-1MP-DNTT The solubility of $C_n$-DNTTs ($C_n$=a linear alkyl chain) are very low in organic solvents (up to ~80 mg/L in toluene at 60° C.) (see: *Adv. Mater.* 2011, 23, 1222-1225). The solubility of 2,9-1MP-DNTT can be about 50 g/L in toluene at 60° C., which is >500 times higher than those of the corresponding linear alkyl chain DNTT compounds having the same (or lower) number of carbon atoms.

EXAMPLE 7

Device Fabrication and Test Procedures

Device Fabrication Procedure (Bottom Gate Top Contact (BGTC)): BGTC TFTs were fabricated using compounds of the present teachings as the semiconductor layer. N-doped silicon wafers (100) with 3000 Å thermally grown silicon dioxide layer (Addison Inc. were used as device substrates. Prior to deposition of the semiconductor, the $Si/SiO_2$ surfaces were modified through a special octadecyltrichlorosilane (OTS) treatment process. Thin films of semiconductors approximately 40-120 nm in thickness were prepared through physical vapor deposition (PVD), with the deposition rate of 0.1-0.5 Å/s and the substrate temperature of 30-120° C. The TFTs were completed by vapor deposition of 300 Å gold source/drain electrodes onto the semiconductor layer through a stencil mask to define the transistor channel. The channel lengths and widths are about 50-200 μm and about 500-2000 μm, respectively. The silicon dioxide layer served as the gate insulator. The gate electrode was accessed through an ohmic contact to the doped silicon.

Device Fabrication Procedure (Top Gate Bottom Contact (TGBC)): For TGBC devices, PolyEthyleneNaphthalate (PEN) substrates (2"×2") were planarized with UV-curable polymeric films (ActivInk D1400, Polyera Corp., Skokie, Ill.). A silver layer of 30 nm was then deposited by thermal evaporation. Source and drain contacts were patterned using photolithography process and silver was etched by a mixture of acids and water. The semiconductor was spun from a hydrocarbon solution (15 mg-mL) at 2000 rpm. The semiconductor film thickness depends on the solubility of the semiconductor. In the case of 2,9-1MP-DNTT, the film had a thickness of about 60 nm. These films were then baked on a hot plate at 110° C. for 10 min to remove residual solvent. The amorphous fluoropolymer CYTOP (CTL-809M, Asahi Glass Corporation) was spun as the top-gate dielectric at 5000 rpm to a thickness of about 450 nm, and baked on a hot plate at about 110° C. for 10 minutes. The device structure was completed by the evaporation of an aligned Ag top-gate stripe.

Device Fabrication Procedure (Bottom Gate Bottom Contact (BGBC)): For BGBC devices, a Cr/Au gate stripe was evaporated on clean PEN substrates. Subsequently, UV-curable polymeric films (ActivInk D1450, Polyera Corp., Skokie, Ill.) were spun (thickness ~500 nm) and cured to form the bottom-gate dielectric. A silver layer of 30 nm was then deposited by thermal evaporation. Source and drain contacts were patterned using photolithography process and silver was etched by a mixture of acids and water. Thin films of the semiconductor were prepared according to the same protocols as for the TGBC devices.

EXAMPLE 8

Transistor Performance Comparison

The TFT performance of 2,9-1MP-DNTT were compared vis-a-vis to that of C8-DNTT (synthesized according to the procedure reported in *Org. Lett.* 2011, 13, 3430) in several device architectures. The results are summarized in Table 1.

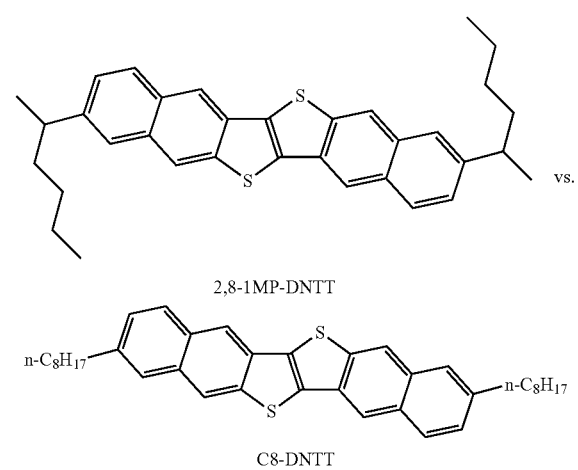

TABLE 1

Summary of average hole mobilities ($\mu_{mean}$), on/off ratios ($I_{ON}/I_{OFF}$), and threshold voltages ($V_T$) for various OTFTs.

| Compound | Device Architecture | Semiconductor Deposition Method[a] | Channel Length (μm) | $\mu_{mean}$ (cm²/V · s) | $V_T$ (V) | $I_{ON}/I_{OFF}$ |
|---|---|---|---|---|---|---|
| 2,9-1MP-DNTT | BGTC | PVD | 50-200[b] | 1-3 | ~0 | ~10⁶ |
| | TGBC | SC | 20[c] | 1.50 | 0 | 8 × 10⁶ |
| | TGBC | SC | 10[c] | 1.01 | +2 | 2 × 10⁶ |
| | TGBC | SC | 5[c] | 0.56 | +5 | 1 × 10⁷ |
| | TGBC | SC | 3[c] | 0.35 | +6 | 2 × 10⁷ |
| | BGBC | SC | 10[c] | 0.70 | 0 | 7 × 10⁶ |
| 2,9-1MB-DNTT | TGBC | SC | 10[c] | 1.80 | +4 | 1 × 10⁷ |
| C8-DNTT (comparison) | BGTC | PVD | 50-200[b] | 1-3 | ~−5 | ~10⁶ |
| | TGBC | SC | 20[c] | inactive | — | — |
| | BGBC | SC | 10[c] | inactive | — | — |
| 2-1MP-DNTT | BGTC | PVD | 100[b] | 2.3 | ~−60 | ~10⁶ |
| 2-1MP-NTTB | BGTC | PVD | 100[b] | 0.3 | ~−25 | ~10⁶ |
| | TGBC | SC | 10[c] | 0.14 | ~−2 | ~10⁷ |
| | BGBC | SC | 10[c] | 0.10 | ~−2 | ~10⁶ |

[a]SC means spin-coating from a solution of the compound that was maintained at or near room temperature (<40° C.).
[b]Electrical contacts are Au.
[c]Electrical contacts are Ag.

Figure 2:
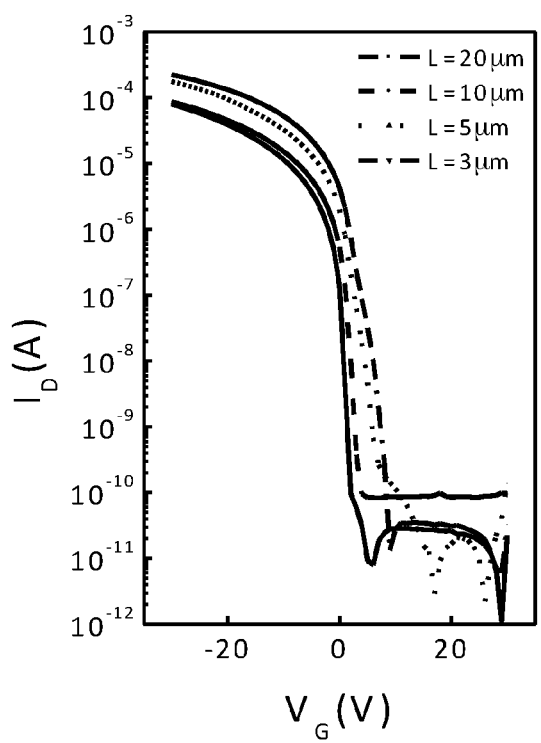
FIG. 2 shows representative transfer plots of 2,9-1MP-DNTT-based OTFT devices (top-gate bottom-contact) at different channel lengths (L).
Figure 3:
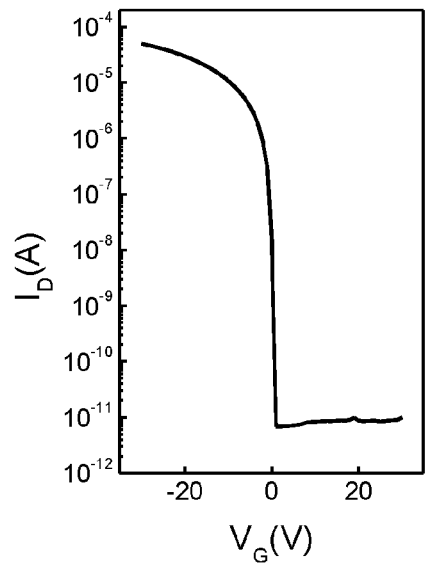
FIG. 3 shows a representative transfer plot of a 2,9-1MP-DNTT-based OTFT device (bottom-gate bottom-contact, L=10 μm).

FIG. 2 shows representative transfer plots of 2,9-1MP-DNTT-based OTFT devices (top-gate bottom-contact) at different channel lengths (L). FIG. 3 shows a representative transfer plot of a 2,9-1MP-DNTT-based OTFT device (bottom-gate bottom-contact, L=10 μm).

All devices were characterized in a Signatone Probe Station using a Keithley 4200 Semiconductor Characterization System to obtain transfer and output characteristics. Device parameters were extracted from the transfer characteristics according to standard transistor equations.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

The invention claimed is:

1. A compound having the formula IIa:

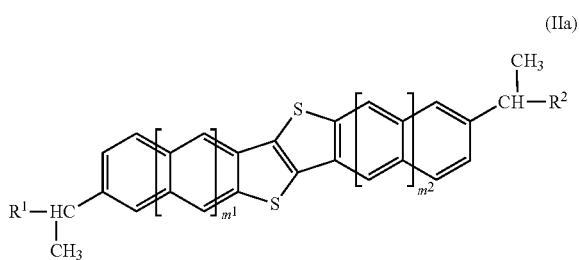

(IIa)

wherein $R^1$ and $R^2$ independently are a linear $C_{4-40}$ alkyl group; and $m^1$ and $m^2$ are 1.

2. The compound of claim 1, wherein the compound has the formula:

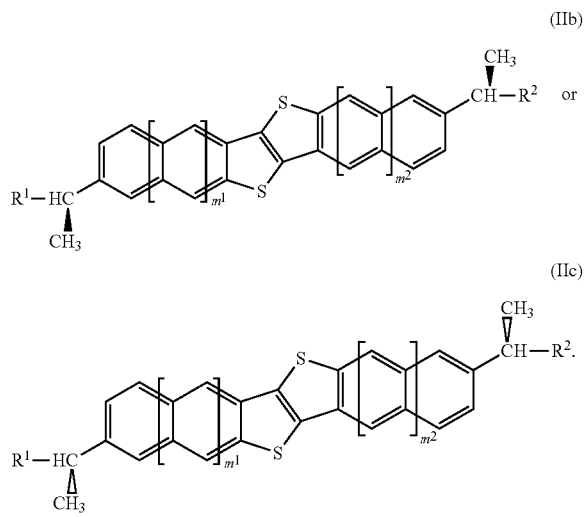

3. The compound of claim 1, wherein $R^1$ and $R^2$ independently are selected from n-$C_4H_9$, n-$C_5H_{11}$, n-$C_6H_{13}$, n-$C_7H_{15}$, n-$C_8H_{17}$, n-$C_9H_{19}$, n-$C_{10}H_{21}$, n-$C_{11}H_{23}$, and n-$C_{12}H_{25}$.

4. A thin film semiconductor comprising a compound of claim 1.

5. An electronic device, an optical device, or an optoelectronic device comprising the thin film semiconductor of claim 4.

6. A field effect transistor device comprising a source electrode, a drain electrode, a gate electrode, and the thin film semiconductor of claim 4 in contact with a dielectric material.

7. The field effect transistor device of claim 6, wherein the field effect transistor has a structure selected from top-gate bottom-contact structure, bottom-gate top-contact structure, top-gate top-contact structure, and bottom-gate bottom-contact structure.

8. The field effect transistor device of claim 6, wherein the dielectric material comprises an organic dielectric material.

9. The field effect transistor device of claim 6, wherein the dielectric material comprises an inorganic dielectric material or a hybrid organic/inorganic dielectric material.

10. A light emitting transistor device comprising a source electrode, a drain electrode, a gate electrode, a dielectric material, and a photoactive component comprising a compound of claim 1, wherein the photoactive component is in contact with the dielectric material.

11. The light emitting transistor device of claim 10, wherein the photoactive component comprises a laminate of two or more layers.

12. The light emitting transistor device of claim 11, wherein the laminate comprises a light emitting layer and one or more organic charge transport layers.

13. The light emitting transistor device of claim 10, wherein the compound of claim 1 is present in a blend material.

* * * * *